(12) United States Patent
Whayne et al.

(10) Patent No.: US 9,943,364 B2
(45) Date of Patent: **\*Apr. 17, 2018**

(54) METHOD AND DEVICES FOR COAGULATION OF TISSUE

(75) Inventors: James G. Whayne, Chapel Hill, NC (US); Sidney D. Fleischman, Durham, NC (US); Christopher W. Sicvol, Durham, NC (US)

(73) Assignee: AtriCure, Inc., Mason, OH (US)

( \* ) Notice: Subject to any disclaimer, the term of this patent is extended or adjusted under 35 U.S.C. 154(b) by 830 days.

This patent is subject to a terminal disclaimer.

(21) Appl. No.: 13/541,580

(22) Filed: Jul. 3, 2012

(65) Prior Publication Data

US 2012/0271299 A1    Oct. 25, 2012

Related U.S. Application Data

(63) Continuation of application No. 12/685,596, filed on Jan. 11, 2010, now Pat. No. 8,241,273.

(60) Provisional application No. 61/143,688, filed on Jan. 9, 2009.

(51) Int. Cl.
| | |
|---|---|
| *A61B 18/18* | (2006.01) |
| *A61B 18/14* | (2006.01) |
| *A61B 18/20* | (2006.01) |
| *A61B 18/12* | (2006.01) |
| *A61B 18/02* | (2006.01) |
| *A61B 18/06* | (2006.01) |
| *A61B 18/08* | (2006.01) |
| *A61B 18/24* | (2006.01) |
| *A61B 17/00* | (2006.01) |
| *A61B 18/00* | (2006.01) |

(52) U.S. Cl.
CPC ...... *A61B 18/1492* (2013.01); *A61B 18/1206* (2013.01); *A61B 18/201* (2013.01); *A61B 18/02* (2013.01); *A61B 18/06* (2013.01); *A61B 18/08* (2013.01); *A61B 18/082* (2013.01); *A61B 18/1402* (2013.01); *A61B 18/18* (2013.01); *A61B 18/24* (2013.01); *A61B 2017/00057* (2013.01); *A61B 2017/00084* (2013.01); *A61B 2018/00351* (2013.01); *A61B 2018/00577* (2013.01); *A61B 2018/00589* (2013.01); *A61B 2018/00809* (2013.01); *A61B 2018/00821* (2013.01); *A61B 2018/126* (2013.01)

(58) Field of Classification Search
USPC .......................................... 606/1–50
See application file for complete search history.

(56) References Cited

U.S. PATENT DOCUMENTS

| | | |
|---|---|---|
| 4,905,698 A | 3/1990 | Strohl, Jr. et al. |
| 5,370,640 A | 12/1994 | Kolff |
| 5,425,367 A | 6/1995 | Shapiro et al. |
| 5,722,426 A | 3/1998 | Kolff |
| 5,906,579 A | 5/1999 | Vander Salm et al. |
| 6,113,588 A | 9/2000 | Duhaylongsod et al. |
| 6,241,667 B1 | 6/2001 | Vetter et al. |
| 6,298,261 B1 | 10/2001 | Rex |
| 6,321,109 B2 * | 11/2001 | Ben-Haim et al. ........... 600/424 |

(Continued)

FOREIGN PATENT DOCUMENTS

| | | |
|---|---|---|
| GB | 2298489 | 9/1996 |
| WO | WO 2008/091610 | 7/2008 |

*Primary Examiner* — John R Downey
(74) *Attorney, Agent, or Firm* — Levine Bagade Han LLP

(57) ABSTRACT

Methods and devices described herein facilitate improved treatment of body organs.

16 Claims, 34 Drawing Sheets

(56) References Cited

U.S. PATENT DOCUMENTS

| | | |
|---|---|---|
| 6,332,089 B1* | 12/2001 | Acker et al. ............... 600/424 |
| 6,463,313 B1 | 10/2002 | Winston et al. |
| 6,669,687 B1 | 12/2003 | Saadat |
| 6,685,666 B1 | 2/2004 | Fontenot |
| 7,273,056 B2 | 9/2007 | Wilson et al. |
| 7,366,562 B2 | 4/2008 | Dukesherer et al. |
| 7,485,098 B2 | 2/2009 | Mitra |
| 7,493,154 B2 | 2/2009 | Bonner et al. |
| 7,530,980 B2* | 5/2009 | Hooven ...................... 606/41 |
| 8,241,273 B2* | 8/2012 | Whayne et al. ............ 606/15 |
| 8,465,479 B2 | 6/2013 | Whayne et al. |
| 2002/0002372 A1* | 1/2002 | Jahns et al. ............... 606/41 |
| 2002/0038120 A1 | 3/2002 | Duhaylongsod et al. |
| 2002/0045811 A1 | 4/2002 | Kittrell et al. |
| 2002/0052597 A1 | 5/2002 | Duhaylongsod et al. |
| 2003/0023236 A1 | 1/2003 | Gowda et al. |
| 2003/0069577 A1* | 4/2003 | Vaska et al. ............... 606/41 |
| 2005/0187545 A1* | 8/2005 | Hooven et al. ............ 606/41 |
| 2006/0122587 A1 | 6/2006 | Sharareh |
| 2006/0184048 A1 | 8/2006 | Saadat |
| 2007/0213617 A1 | 9/2007 | Berman et al. |
| 2007/0287886 A1 | 12/2007 | Saadat |
| 2008/0058649 A1 | 3/2008 | Boyden et al. |
| 2008/0058785 A1 | 3/2008 | Boyden et al. |
| 2008/0058786 A1 | 3/2008 | Boyden et al. |
| 2008/0058788 A1 | 3/2008 | Boyden et al. |
| 2008/0058795 A1 | 3/2008 | Boyden et al. |
| 2008/0059070 A1 | 3/2008 | Boyden et al. |
| 2008/0103355 A1 | 5/2008 | Boyden et al. |
| 2008/0275440 A1 | 11/2008 | Kratoska et al. |
| 2008/0281312 A1 | 11/2008 | Werneth et al. |
| 2010/0010488 A1 | 1/2010 | Kassab et al. |
| 2010/0179524 A1 | 7/2010 | Whayne et al. |
| 2010/0217249 A1 | 8/2010 | Whayne et al. |

\* cited by examiner

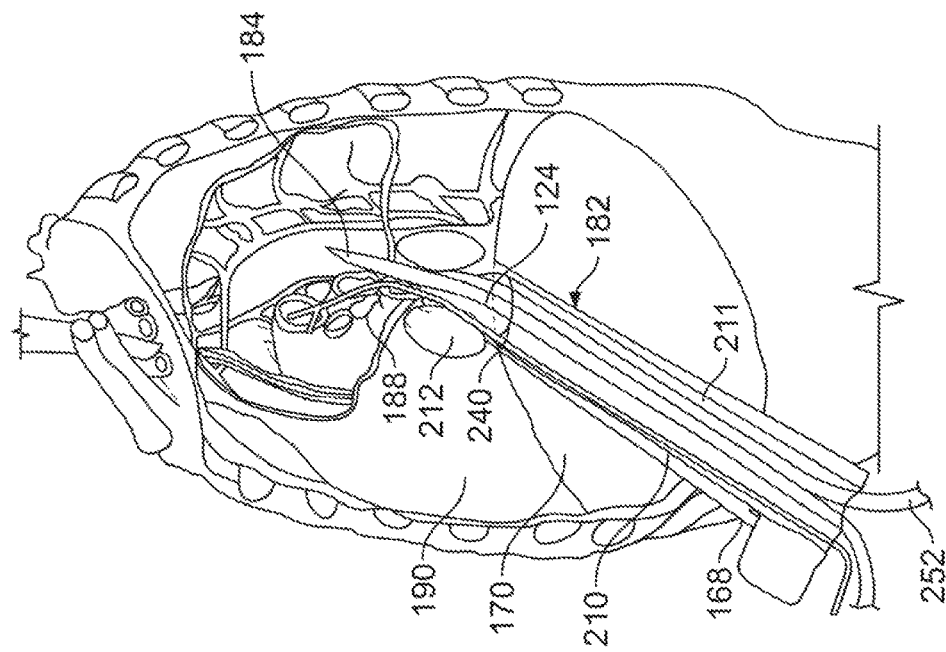
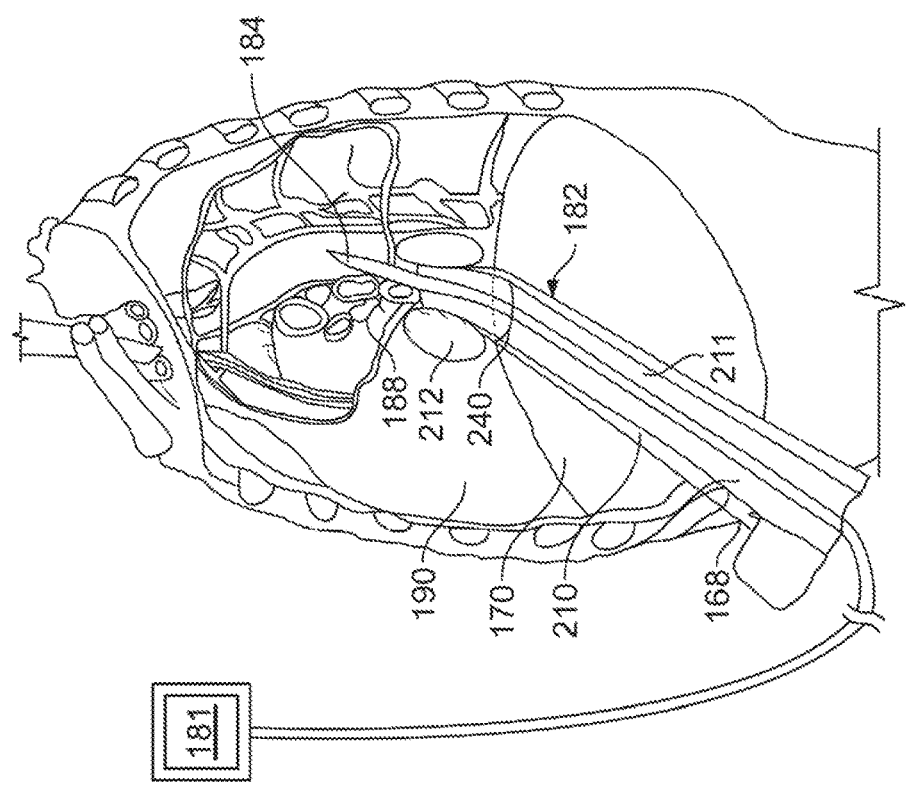

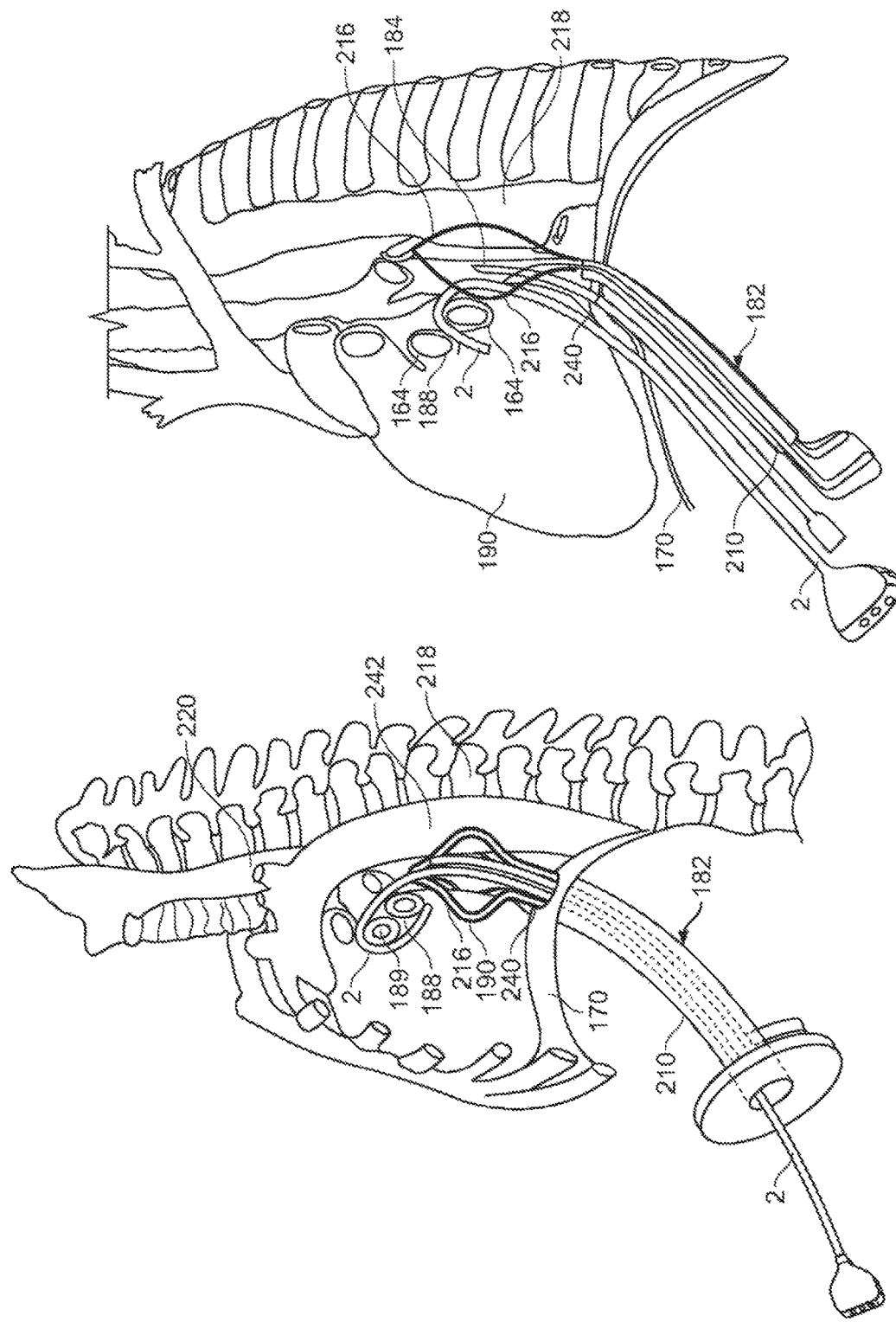

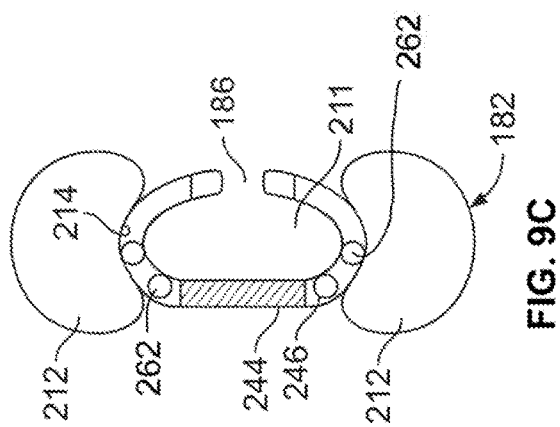
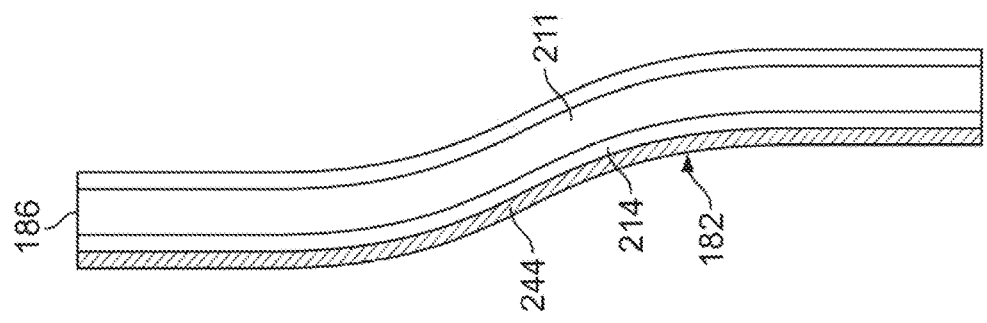
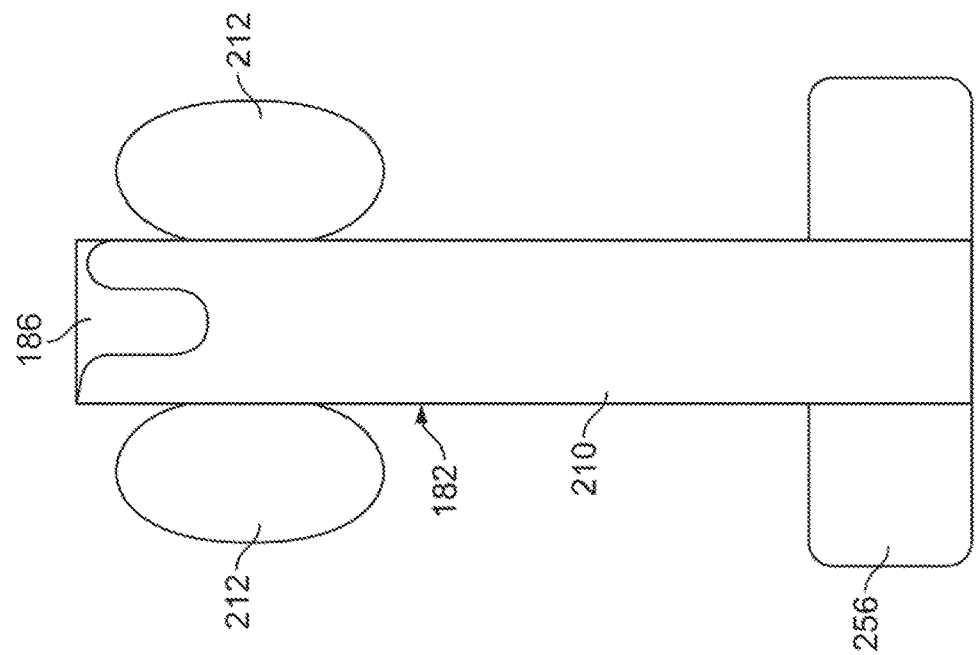

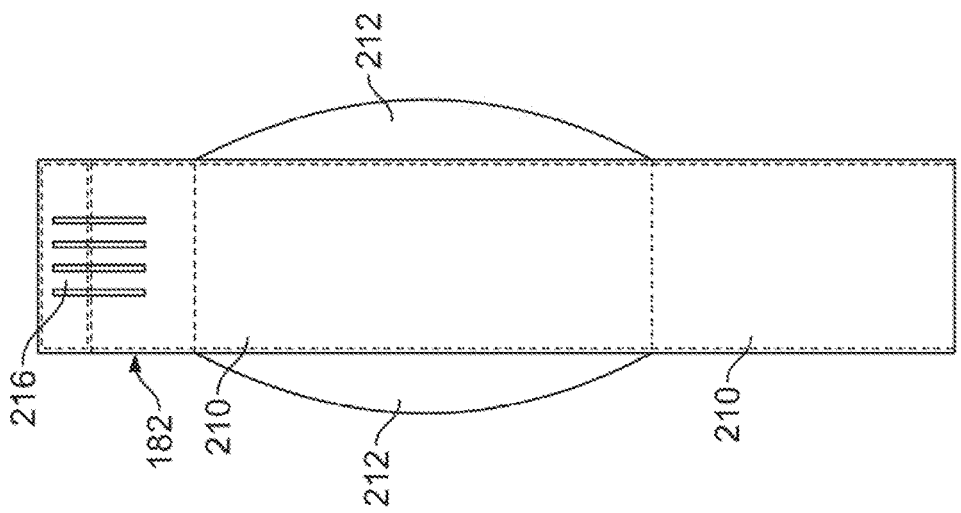
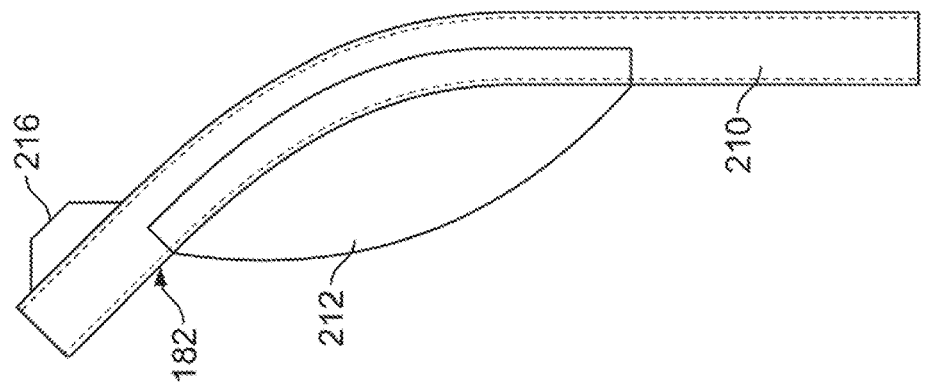
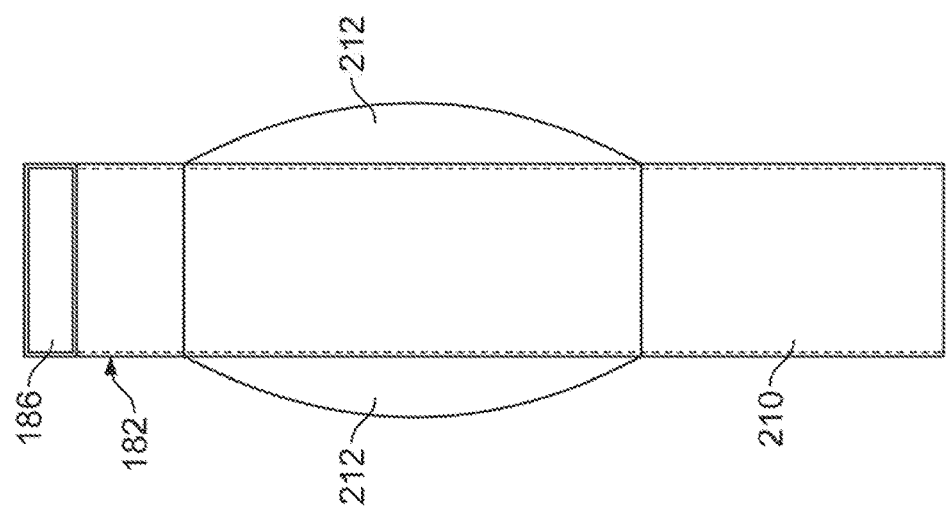

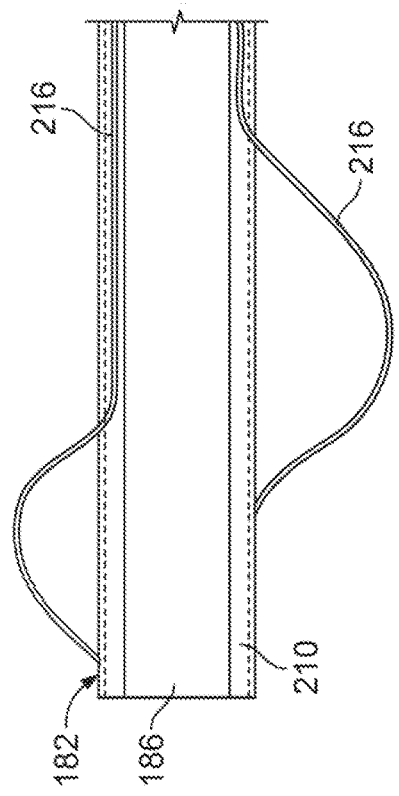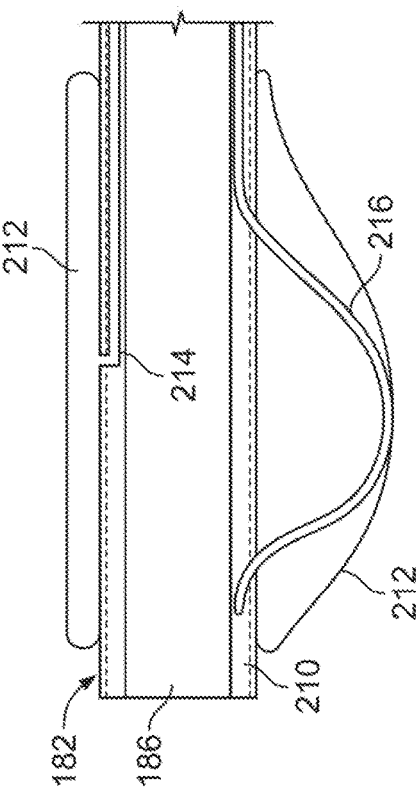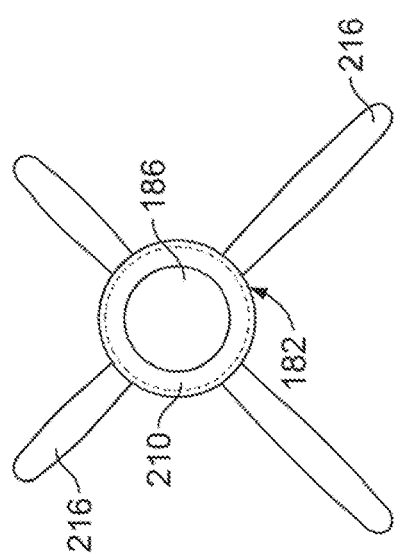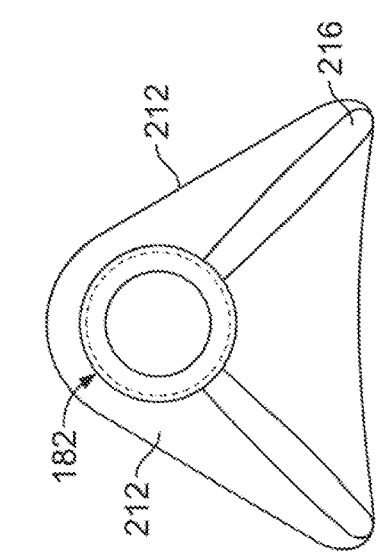
FIG. 11B
FIG. 11D
FIG. 11A
FIG. 11C

METHOD AND DEVICES FOR COAGULATION OF TISSUE

This application is a continuation of U.S. patent application Ser. No. 12/685,596 filed Jan. 11, 2010 which is a non-provisional of U.S. Provisional Application No. 61/143,688 filed Jan. 9, 2009 entitled "Minimally Invasive Lesion Pattern and Dissecting Instruments Utilizing Endocardial and Epicardial Lesions". The above filings are hereby incorporated by reference in its entirety.

BACKGROUND OF THE INVENTION

Field of the Inventions

Methods and devices are disclosed herein for therapeutically treating tissue. In one example, the devices and methods are suitable for minimally invasive surgery. More particularly, methods and devices described herein permit creating an ablation pattern on an organ while reducing excessive trauma to a patient. The methods and devices also allow for improved access within a body cavity to perform a surgical procedure, for example ablation and/or coagulation of cardiac tissue during minimally invasive surgical access to the heart.

Description of the Related Art

Atrial fibrillation surgery requires creation of an ablation or coagulation lesion in atrial tissue. Typically, a physician creates a lesion using energy (including but not limited to radiofrequency, D.C., microwave, laser or other thermal modalities) to prevent wavelets or electrical signals/impulses that propagate through the atrial tissue to sustain atrial fibrillation or produce atrial flutter, atrial tachycardia, or other arrhythmia.

Many conventional approaches in applying energy to the atrial tissue face difficulties in attempting to create a complete lesion pattern that prevents propagation of the electrical impulse across the lesion pattern. Some factors attributable to these difficulties are tissue contact throughout the length of the electrode(s) is/are not consistent causing variability in the transmission of energy throughout the target length of ablated/coagulated tissue. Moreover, surrounding anatomic features also contributes to the difficulty in creating a complete lesion pattern. As a result, an incomplete lesion or lesion pattern includes one or more gaps of viable or semi-viable tissue that allows propagation of wavelets through tissue and through the lesion pattern.

Another factor in the inability of existing thermal ablation systems to create complete curvilinear, transmural lesions is the presence of convective cooling on the opposite surface of the atrium. This convective cooling produces a heat sink that decreases the maximum temperature at this surface thereby preventing the lesions from consistently extending transmurally through the entire wall of the atrium. This is especially relevant during beating-heart procedures in which the coagulation/ablation probe is placed against the epicardial surface, and blood flowing along the endocardium removes heat thus producing a larger gradient between temperature immediately under the electrodes along the epicardium and that the temperature at the endocardium.

Yet another other deficiency of current approaches is the inability to direct the coagulation of precise regions of soft tissue while avoiding underlying or nearby tissue structures. For example, atrial fibrillation ablation may involve extending a lesion to the annulus near which the circumflex, right coronary artery, and coronary sinus reside; another example involves ablating ventricular tachycardia substrates that reside near coronary arteries or coronary veins. Conventional approaches are unable to selectively ablate desired soft tissue structures and isolate preserved tissue structures from targeted regions.

Traditionally, atrial coagulation patterns were only completed using endocardial coagulation lesions. In such procedures, the physician introduced one or more intravenous catheters through the vasculature to atrial tissue. Endocardial coagulation suffers a drawback in that the physician cannot easily visualize the site being ablated. Furthermore, endocardial coagulation carry a risk of complications due to ablating outward from the endocardial surface including esophageal fistula, thromboembolic complications from coagulum formation, PV stenosis, phrenic nerve palsy and lung damage. Aside from the risks, it is difficult to create complete linear lesion lines via an endocardial approach.

Recently, systems have been developed to ablate the cardiac tissue on the epicardium. Epicardial coagulation allows for more comprehensive bi-atrial lesion patterns at the expense of procedural complexity and time. However, many current procedures require significant manipulation of other tissue structures to create the desired lesion pattern. For example, many procedures require one or more ports or trocars placed in a chest wall and/or deflation of a lung to access the target site. Furthermore, many existing procedures require dissection of pericardial reflections to create a full lesion pattern. Dissection of these pericardial reflections presents many additional complications. For example, the tissue surrounding the reflections is very delicate and can be easily damaged during creation of the lesion, or when dissecting the reflection. Visualization is difficult during dissecting of a pericardial reflection so any inadvertent dissection out-of-plane could cause dissection of other tissue structures. For instance, inadvertent dissection of a pulmonary vein can obviously cause significant harm to a patient.

A convergent coagulation pattern utilizes both endocardial and epicardial lesions provide a technique that is comprehensive, bi-atrial and simpler than an epicardial or endocardial procedure alone. In one variation of this convergent procedure, a physician is able to accurately determine the perimeter or outline of a lesion on one side of tissue from an opposite side of the tissue. This allow for improved placement of the lesions and produces the convergent coagulation pattern without creating significant gaps that allow electrical impulses to pass therethrough in tissue.

The improved methods and devices described herein offer improved access to tissue regions within the body, especially those organs in the thoracic cavity. Variations of these methods and devices address the above described deficiencies for atrial fibrillation and ventricular tachycardia ablation. In addition, the embodiments or variations of the embodiments may address similar deficiencies, which are apparent during other applications involving coagulation of a selected tissue region in a precise manner.

SUMMARY OF THE INVENTION

The devices described herein allow for creation of bi-atrial lesion patterns on opposing cardiac surfaces. However, the methods and techniques are applicable to non-cardiac treatments as well.

One method according to the present disclosure includes coagulating cardiac tissue, where the cardiac tissue comprises a first cardiac surface and a second cardiac surface, where the second cardiac surface is on an opposite side of the cardiac tissue from the first cardiac surface. The opposite side generally includes the interior and exterior surface of the tissue. In this manner a coagulation lesion created on an exterior surface can be effectively contiguously formed with a lesion created on an interior surface to extend the electrical blocking effect of each lesion across the contiguous lesion. In the following disclosure, the term cardiac tissue, unless specifically indicated otherwise, shall include any tissue that is treated or observed during a cardiac coagulation/ablation procedure. For example, cardiac tissue could include ventricular and atrial surfaces as well.

In one variation, the method includes positioning a first coagulation device adjacent to the first cardiac surface; forming a first coagulation lesion along the first cardiac surface using the coagulation device such that the first coagulation lesion forms an electrical barrier that prevents an electrical impulse from propagating in cardiac tissue across the first coagulation lesion; positioning a second device having at least one electromagnetic energy source adjacent to the second cardiac surface; applying electromagnetic energy adjacent to the second cardiac surface using the electromagnetic energy source; identifying a location of the electromagnetic energy through the cardiac tissue from the first cardiac surface to locate the second device; and repositioning the second device at a target location on the second cardiac surface in response to the location of the first coagulation lesion.

The method can further include creating a second coagulation lesion along the second cardiac surface, where the second coagulation lesion extends the electrical barrier of the first coagulation lesion to form a contiguous lesion.

The method described below allow for a variation of a procedure where creation of the lesion creates the electrical barrier across cardiac tissue without dissecting a pericardial reflection.

The source of coagulation energy in any of the variations described herein can include RF energy, a laser energy, an infrared heat, a chemical energy, cryogenic energy, a microwave energy, and a resistive heating as well as other coagulation or ablation modalities. In addition, the electromagnetic energy can include visible light, coherent light, ultraviolet light, magnetic energy, and electrical energy.

In one variation the first cardiac surface comprises an epicardial surface and the second cardiac surface comprises an endocardial surface. However, an alternative variation allows for the creation of the lesion pattern to be reversed. In such a variation the first cardiac surface comprises an endocardial surface and the second cardiac surface comprises an epicardial surface.

The methods of accessing the thoracic cavity include use of a port or trocar located in an abdominal wall of the body where the first coagulation device is advanced through the diaphragm. Alternatively, or in combination, the port or trocar is located in a chest wall of the body and the first coagulation device is advanced through the diaphragm and pericardium into the pericardial space.

In another variation, the method further includes advancing a scope into a body where the scope comprises at least one visualization element and where identifying the location of the electromagnetic energy through the cardiac tissue from the first cardiac surface to locate the second device comprises using the visualization element to identify the location of the electromagnetic energy.

Another method according to the following disclosure includes coagulating tissue to create a bi-atrial coagulation pattern on a first and a second atrial surfaces where the first atrial surface and the second atrial surface are located on opposite sides of the cardiac tissue. In one variation, the method comprises positioning a first coagulation device adjacent to the first atrial surface of the cardiac tissue; creating a first partial coagulation pattern on the first atrial surface with the first coagulation device, where the first partial coagulation pattern comprises at least a first plurality of lesions where at least two of the first plurality of lesions are separated by a gap section, where the gap section allows an electrical impulse to flow therethrough in the cardiac tissue; positioning a second coagulation device adjacent to the second atrial surface of the cardiac tissue; and creating a second partial coagulation pattern on second surface with the second coagulation device, where the second partial coagulation pattern comprises at least one lesion across the gap to form the complete coagulation pattern such that the electrical impulse cannot flow across the complete coagulation pattern.

A variation of this method can include determining a position of the second coagulation device through the cardiac tissue from the first atrial surface.

The method can include applying a locational energy at the second atrial surface in an amount insufficient to ablate or coagulate tissue and observing the locational energy from the first atrial surface to determine the position of the second coagulation device. In certain variations, this locational energy is contrasted from ablation or coagulation energy, as the locational energy does not significantly affect the tissue. However, alternative variations of the method can include increasing the intensity or power of the locational energy to sufficiently create a coagulation or ablation lesion.

In an additional variation, the scope comprises at least one visualization element configured to observe the locational energy from the first atrial surface and where positioning the second coagulation device comprises moving the second coagulation device in response to observing the locational energy.

Another variation of methods under the present disclosure includes a method of creating a contiguous lesion pattern in a body, the contiguous lesion pattern comprising multiple lesions on both an interior cardiac surface and an exterior cardiac surface, where the interior and exterior cardiac surfaces are located on opposite sides of a cardiac tissue. One variation of such a method can include creating an interior coagulation lesion on an interior cardiac surface; monitoring the exterior cardiac surface for change in the cardiac tissue to identify the location of the interior coagulation lesion on the interior cardiac surface; creating an exterior coagulation lesion on the exterior cardiac surface; where monitoring the exterior cardiac surface allows placement of the interior coagulation lesion and exterior coagulation to overlap, intersect, and/or join and form the contiguous coagulation lesion pattern such that an electrical impulse travelling in the cardiac tissue cannot cross the contiguous lesion pattern.

Another method includes forming a contiguous coagulation lesion in a tissue of a heart on multiple but opposite atrial surfaces. Such a method can include positioning a first coagulation device adjacent to an endocardial surface of the tissue; forming an endocardial coagulation lesion with the first coagulation device; determining a location on the epicardial surface of the tissue that corresponds to an end of the endocardial coagulation lesion formed on the endocardial surface; positioning a second coagulation device at or near the location on the epicardial surface such that creating an epicardial coagulation lesion on the epicardial surface causes the lesions to overlap; intersect, and/or join to form the contiguous coagulation lesion such that an electrical impulse is prevented from flowing in the across the contiguous coagulation lesion.

In another variation, a method includes creating a cardiac coagulation pattern in cardiac tissue using a minimally invasive surgical technique by positioning a first coagulation device adjacent to a first cardiac surface; partially forming the cardiac coagulation pattern by applying energy to the first coagulation device to create at least a first plurality of coagulation lesions along the first cardiac surface, where the first plurality of coagulation lesions includes at least two spaced lesions to define a gap section of tissue such that an electrical impulse is able to flow between the two spaced lesions through the gap section of tissue; positioning a second coagulation device adjacent to a second cardiac surface, where the second cardiac surface is on an opposite side of the first cardiac surface; and fully forming the cardiac coagulation pattern by applying energy to the second coagulation device to create at least one bridging coagulation lesion to span the gap section of tissue along the second cardiac surface, where the bridging coagulation lesion prevents an electrical impulse from flowing across the gap section of tissue.

The present disclosure also includes a tissue coagulation device suitable for creating a portion of the bi-atrial lesion. Such a device can include a shaft having at least one coagulation element at a distal portion, where the coagulation element is coupleable to a coagulation power supply; and an illumination source located on an exterior surface of the distal portion of the shaft and coupleable to an illumination power supply.

In one variation, the illumination source comprises an optical fiber extending through a portion of the flexible shaft. However, the illumination source can also comprise a LED or other light source located at a tip of the device. Additional variations include a source of coherent light, a source of visible light.

Methods are also described herein for advancing an access device through a diaphragm. In such a case, the device is advanced through a first incision in an abdomen of the patient creating an opening in the diaphragm, and advancing the access device through the diaphragm into the thoracic cavity. The methods include use of a visualization system coupled to the working channel or inserting a scope-type device into the working channel to provide visual access to the posterior surface of the organ.

The methods described herein include creating a temporary cavity on surfaces of the heart where the access device is placed in the thoracic cavity between the heart and spine. The temporary cavity may be formed on other organs such as an esophagus, and actuating the expandable member to separate the esophagus from esophageal vessels.

A guide wire may be used to assist in positioning the coagulation device. In some variations, additional access ports may be required to assist in placement and visualization of the coagulation patterns. In one such case, access ports can be placed in the right chest to accomplish such a purpose. Alternatively, the diaphragm access may be the sole entry into the thoracic cavity and any number of coagulation devices can be accessed through an access device to create the desired coagulation pattern. The use of the diaphragm entry procedure and devices allow the medical practitioner to avoid dissection of pericardial reflections or minimize the number of pericardial reflections to create a desired coagulation lesion.

Variations of the devices, methods and procedures described herein include combinations of features of the various embodiments or combination of the embodiments themselves wherever possible.

BRIEF DESCRIPTION OF DRAWINGS

FIGS. 7A to 7C show side sectional views of a thoracic cavity with a variation of an access device used to separate the heart from posterior anatomy;

FIGS. 8A to 8C show side views of a thorax with a device as described herein defining a temporary cavity through which surgical devices may be manipulated during a surgical procedure;

FIGS. 9A to 9C show a top view, a side-sectional view, and a cross-sectional view of an variation of an access device for use as described herein;

FIGS. 10A to 10C show a top view, a side view, and a bottom view of another variation of an access device;

FIGS. 11A to 11D show front and side-sectional views of an access device using stabilizer members and stabilizer members within a balloon;

DETAILED DESCRIPTION

Methods and devices described herein provide for creating an ablation or coagulation pattern on an exterior and interior atrial surface. The coagulation pattern comprises any number of coagulation lesions that are contiguous such that the lesions overlap, intersect, and/or join. In one variation, the contiguous lesion forms a barrier to prevent any electrical signal from propagating through or across the lesion pattern. The techniques involved in creating a bi-atrial lesion pattern can be applied to other organs or structures of the body. Accordingly, unless specified otherwise, the methods and devices are not limited to use in cardiac structures.

The methods and devices described herein can be used with conventional approaches for accessing and positioning a coagulation device adjacent to endocardial as well as those techniques for positioning a coagulation device adjacent to epicardial tissues. However, positioning of the coagulation device in an endocardial application can also employ various techniques that allow for improved manipulation of organs and/or instruments in the thoracic cavity. These improved techniques allow for direct visualization along the posterior region of the heart and other anatomic structures not attainable with conventional thoracic approaches. In one instance, the access devices described herein can be combined with a rail-member for accurate positioning of treatment devices over tissue.

Figure 1B:
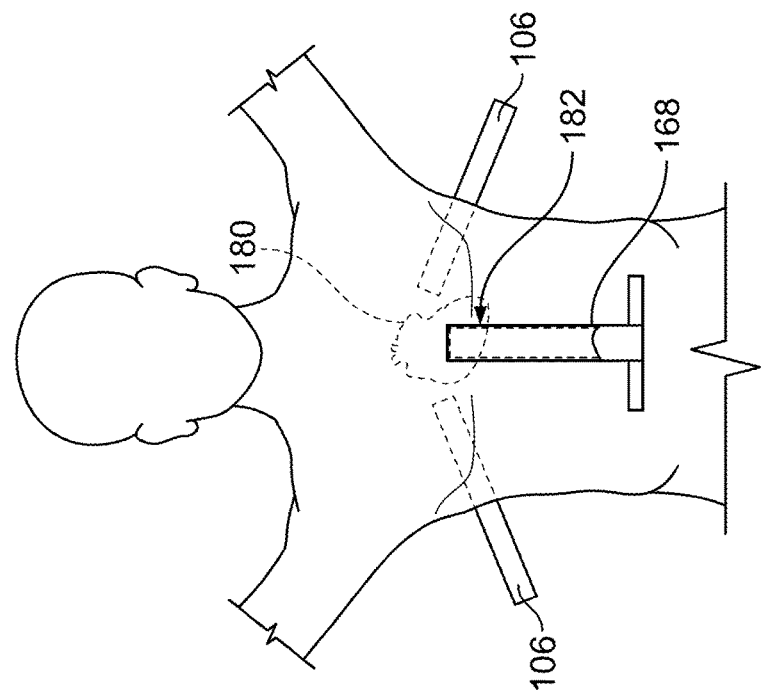
FIGS. 1A and 1B illustrate various approaches for inserting devices to access the heart for performing a bi-atrial lesion pattern.
Figure 1A:
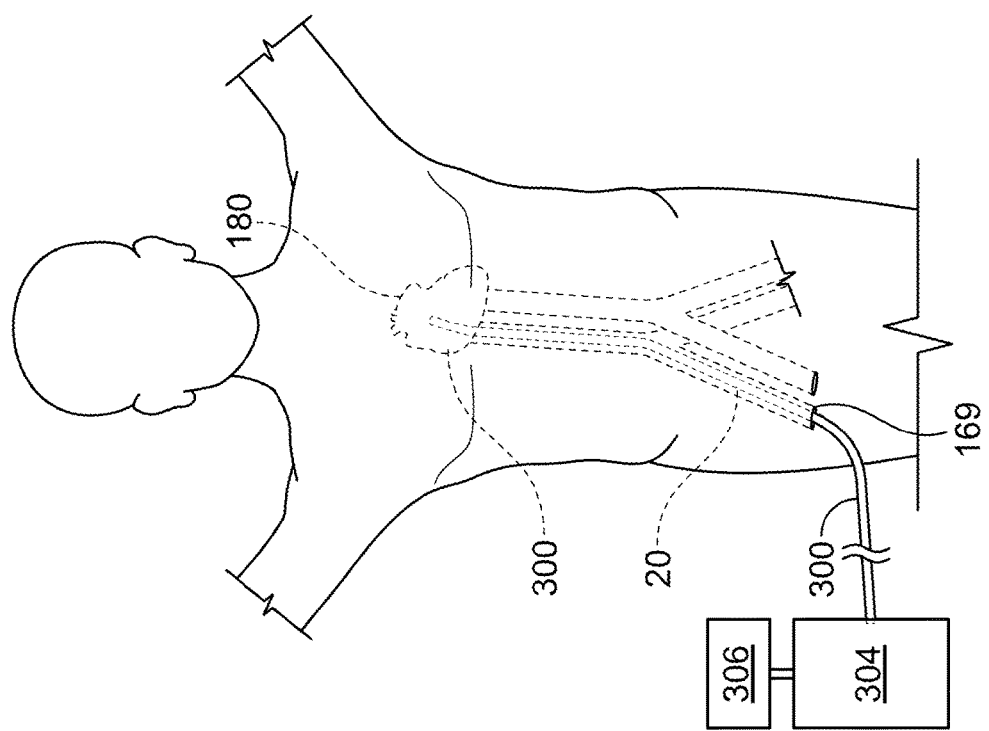
Figure 1C:
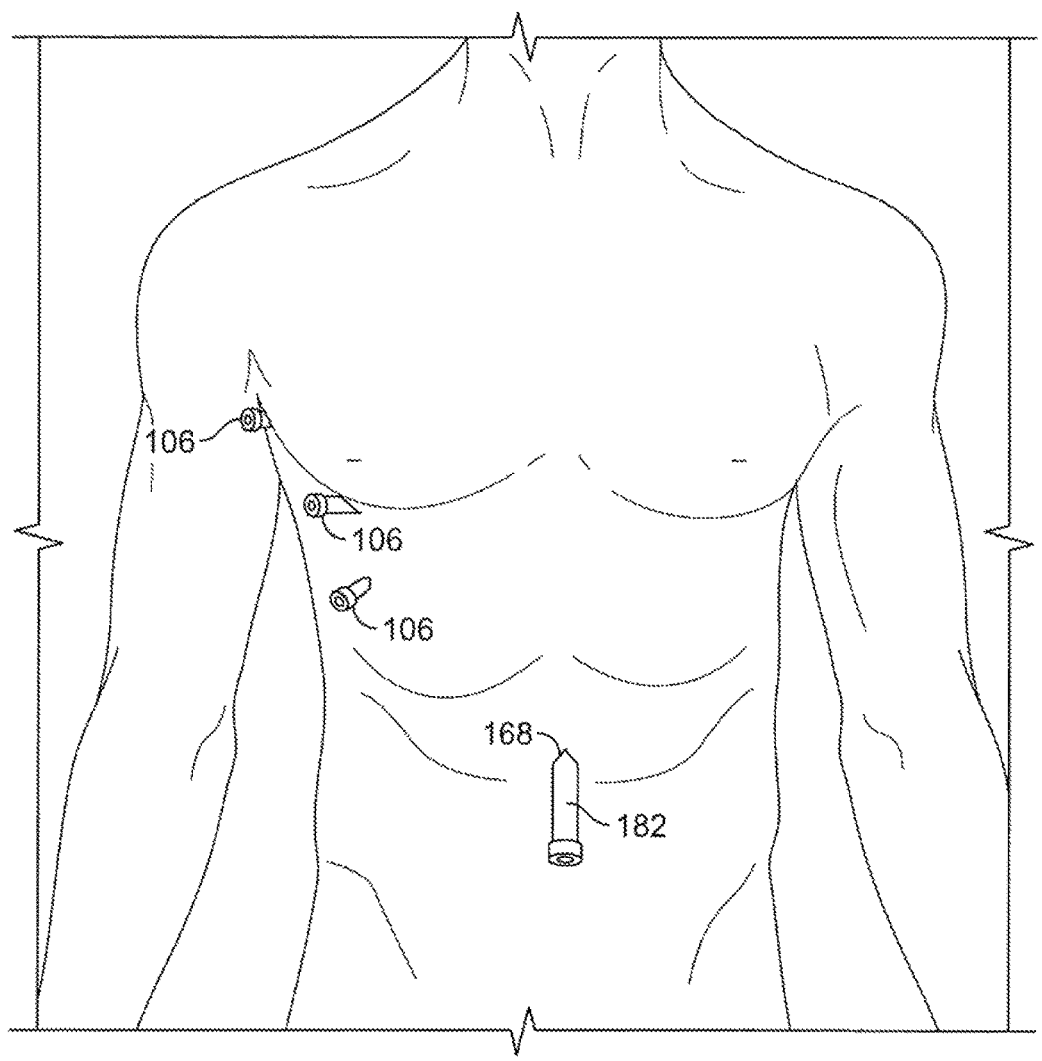
FIG. 1C shows a variation of insertion of an access device to achieve the diaphragm access technique described herein for use with a bi-atrial lesion pattern. In this variation, optional ports can be inserted to provide access to the right side of the thoracic cavity.

FIGS. 1A to 1C illustrate various approaches for inserting devices to access the heart for performing a bi-atrial lesion pattern. FIG. 1A illustrates an example of inserting a device 300 device through an incision 169 in the leg and into a femoral vein 20. In this example, the physician advances the device 300 into a right atrium 195 of the heart 180 to access the endocardial surface for treatment. As will be described herein, the device 300 can comprise a coagulation device that is configured to allow location of the working end of the device, when placed within the heart, from an endocardial or exterior surface of the heart. In alternate variations, the sole function of the device 300 could be to allow for location of the working end of the device. For example, the device 300 could comprise a coagulation device configured to allow for location of the working end from an endocardial surface. In another variation, the device 300 could comprise a guide wire or catheter that can be advanced within the heart, located, and used to deliver a separate coagulation device once a suitable location is identified.

The access procedure shown in FIG. 1A is for exemplary purposes only. Any access procedure that places a coagulation device in proximity to an endocardial location can be employed when the present procedures and methods are used for a cardiac treatment.

FIG. 1A also illustrates the device 300 as being coupled to a power supply 304. The power supply can optionally include hardware or a power supply for determining the location of a working end of the device 300 within the heart from an exterior or endocardial surface as described below. Optionally, this hardware or power supply can be separately coupled via a separate power supply 306. In such a case, the hardware 306 can be applied to conventional devices that would otherwise not be suitable to create a bi-atrial lesion pattern.

FIGS. 1B and 1C show examples of placement of access devices 182 (also referred to as a separator or an elevator herein) as well as trocars 106 for accessing an epicardial surface of the heart 180. Again, the procedure can include a conventional thoracic approach using trocars 106 or ports placed directly into the thoracic cavity. In an additional variation of the methods described herein, thoracic access can be obtained via an abdominal approach. This approach allows for improved posterior access of organs within the thoracic cavity.

In one variation, an access technique includes advancing an access device through an abdominal incision to create an access path to a thoracic cavity. Once a patient is prepared, as shown in FIG. 1B, an access device 182 is inserted through, at least a first, an abdominal, incision 168. The device is then advanced through the diaphragm (not shown) and placed adjacent or between organs for creation of a temporary cavity. FIG. 1B illustrates one example, in this variation; the surgeon places the access 182 between heart and the spine such that the esophagus can be separated from the posterior surface of the heart.

It is important to note that the convergent coagulation pattern disclosed herein can be made without the use of any incisions into the chest wall to access the thoracic cavity, any lung deflation, or any dissections of the pericardial reflections. Instead, a variation of the procedure includes access of the pericardial space via an abdominal approach as disclosed below. However, alternate variations of the procedure and methods described herein can be augmented with one or more additional thoracostomy incisions or punctures allowing for placement of trocars 106 into the thoracic cavity. The trocars 106 permit insertion of surgical tools or visualization devices. Accordingly, the access device 168 allows for direct visualization of the posterior surface of the organs during manipulation of the instruments inserted through the right and/or left thoracostomy access ports 106. Moreover, use of the additional thoracostomy access sites with the access device 168 may permit the surgeon to visualize the anterior surfaces of anatomic structures, during the procedure. Once tissue obscures the surgical site from the surgeon's view via the thoracostomy access ports 106, the access device 168 allows the surgeon to have a posterior view of the surgical site. In some variations, the access device 168 is used alone without the additional thoracostomy access ports 106.

Figure 2A:
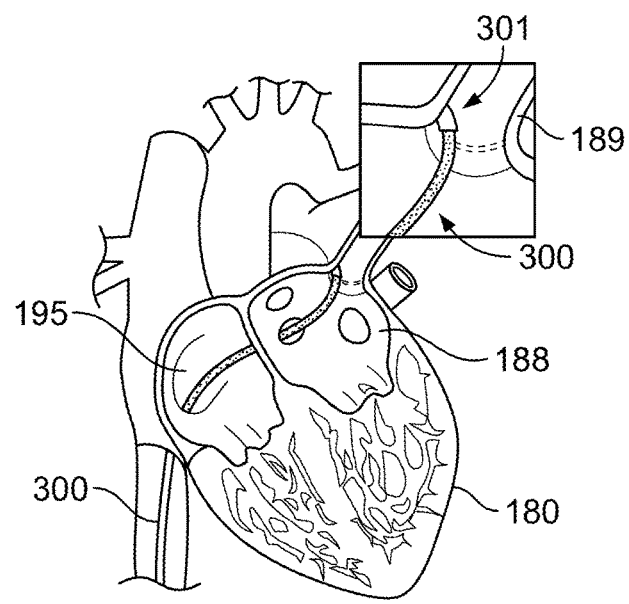
FIG. 2A illustrates an example of advancing the device into a heart for determining a location of the device from an exterior of the heart.

FIG. 2A illustrates an example of advancing the device 300 into a right atrium 195 across a septum and into the left atrium 188 to a pulmonary vein 189. In the illustrated variation, the device 300 comprises a visual light source at a working end 301. However, various other modalities can be employed to determine the location of the working end 301 from the exterior of the heart. As shown in FIG. 2A, a physician can advance the working end 301 of the device against or adjacent to tissue. A steerable sheath or device can be used to position the working end 301 where desired. Alternatively or in combination, the device 300 itself can have a steering mechanism or can be otherwise positionable.

Figure 2B:
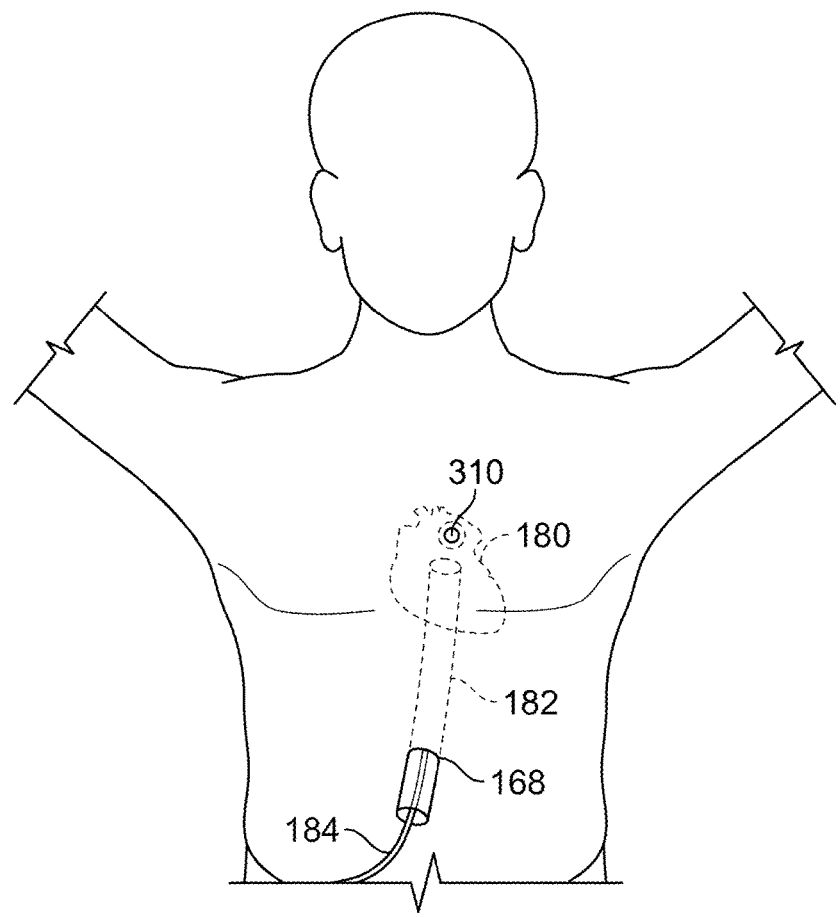
FIG. 2B represents an example of viewing the heart and observing an indicator of the position of the device within the heart where the observation occurs from the thoracic cavity and epicardial surface.

FIG. 2B represents an example of viewing the heart 180 from the thoracic cavity and epicardial surface. As shown, when the working end 301 of the device 300 is advanced against or near tissue on the interior atrial surface, the physician can observe an indication 310 from the epicardial surface. Here, the device 300 applies a locational energy to produce the indication 310. In one variation of the procedure, the physician observes the indication 310 using an access device 182 as described herein that is advanced through an abdominal incision, through the diaphragm and into the pericardial space. A scope 184 (either a separate scope or one that is integrated into the access device 182) allows the physician to visualize the indication 310. In this variation, the physician does not need to place additional access devices, ports, trocars or other similar means in the chest to access the pericardial space. Instead, the entire convergent coagulation pattern is performed via abdominal and vascular access.

In certain variations, this locational energy is contrasted from ablation or coagulation energy as the locational energy does not significantly affect the tissue. However, alternative variations of the method can include increasing the intensity or power of the locational energy to sufficiently create a coagulation or ablation lesion.

Although, FIG. 2A illustrates the working end 301 of the device 300 in a pulmonary vein, for sake of illustration, FIG. 2B shows the working end within the left atrium of the heart. Since the observation is real-time, the physician can reposition the working end 301 of the device 300 as desired. For example, the physician can reposition the working end 301 until the indication 310 shows that the position of the working end 301 on an endocardial surface is adjacent to an existing coagulation lesion on the epicardial surface.

Figure 3A:
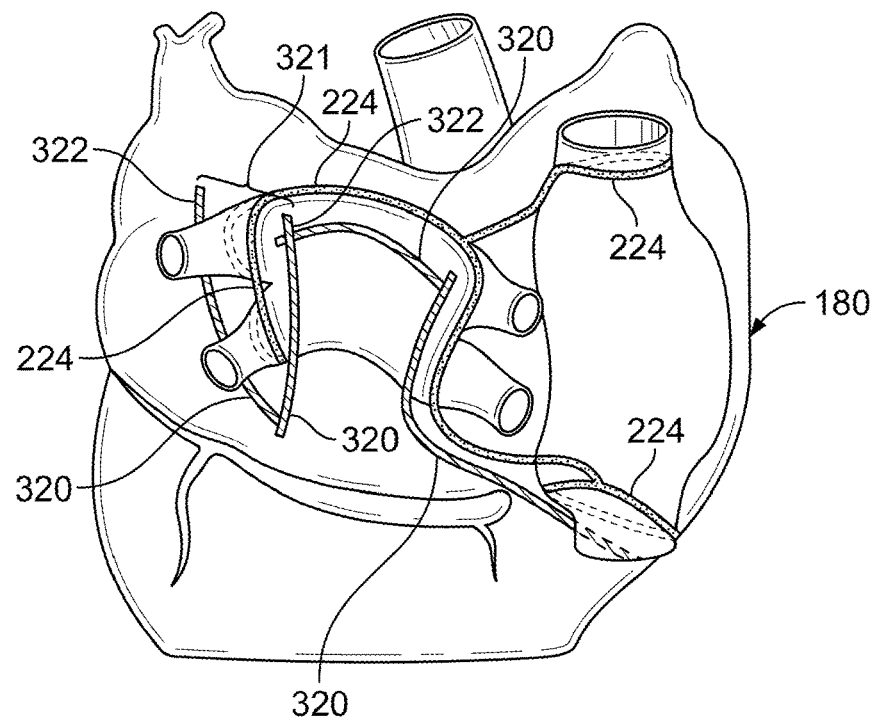
FIGS. 3A to 3E illustrate an example of creating a bi-atrial lesion pattern on a posterior surface of the heart.

FIGS. 3A to 3E illustrate an example of creating a bi-atrial lesion pattern on a posterior surface of the heart 180. FIG. 3A illustrates a posterior surface of the heart showing the various anatomic structures, including pericardial reflections 224 as well as the contoured surfaces and presence of the cardiac structures. These anatomic structures make the creation of a full coagulation pattern a difficult task. FIG. 3A shows partial coagulation pattern created on an epicardial surface of the heart 180. Various devices and methods to access the posterior surface and create the partial lesion pattern are discussed below. As shown, the partial coagulation pattern comprises a number of coagulation lesions 320 that intersect to provide an electrical barrier to prevent electrical impulses or wavelets from propagating in tissue and across the lesion. However, FIG. 3A also illustrates the condition where a gap 321 exists between ends 322 of a pair of lesions 320. In order to complete the coagulation pattern and fully electrically isolate tissue, the physician would be required to dissect pericardial reflections 224 along the epicardial surface and place a coagulation lesion across the gap. However, dissecting the pericardial reflections increases procedure time and causes increased risk during the procedure as discussed above.

Figure 3B:
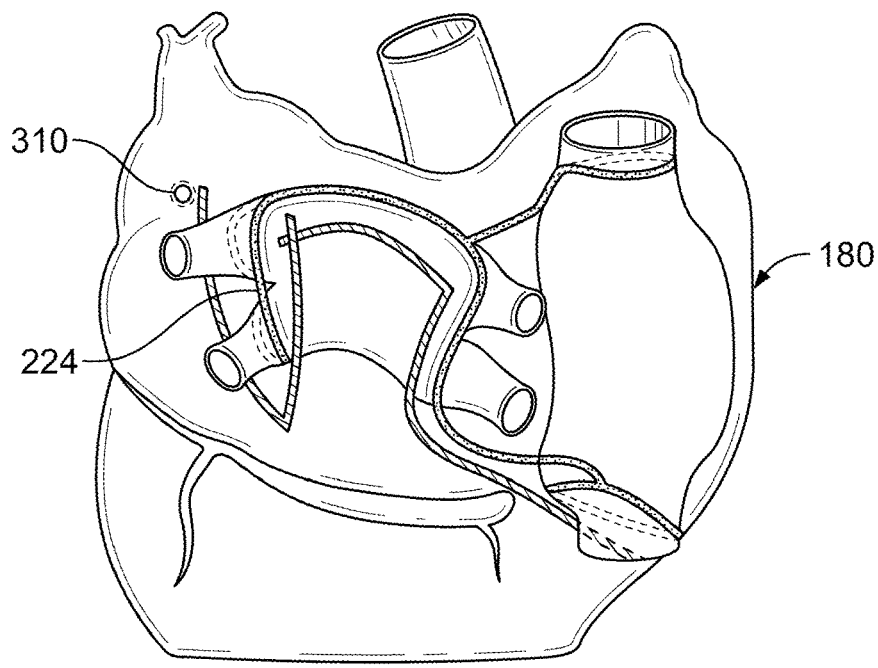

FIG. 3B illustrates the state where the physician advances a device into the chamber of the heart 180 via a vascular approach (similar to that shown in FIG. 2A). As discussed herein the device can comprise a sensor or other source of electromagnetic energy. The device is then advanced against or close to an endocardial surface within the heart. The sensor or source of energy is then actuated to allow a physician to observe the location of the device through the tissue. In the example shown, the physician observes the epicardial surface for an indicator 310 that represents the location of the device within the heart. Once the physician is satisfied that the location of the internal device is positioned to sufficiently form an endocardial coagulation lesion that would overlap, intersect, cross, or otherwise join to one of the epicardial lesions 320, the physician can begin to make an endocardial lesion across the gap section 321 and close or complete the ablation pattern. In this manner, the endocardial lesion and the epicardial lesion form a contiguous lesion that prevents an electrical impulse from propagating in the tissue through the pattern defined by the contiguous lesion.

Figure 3C:
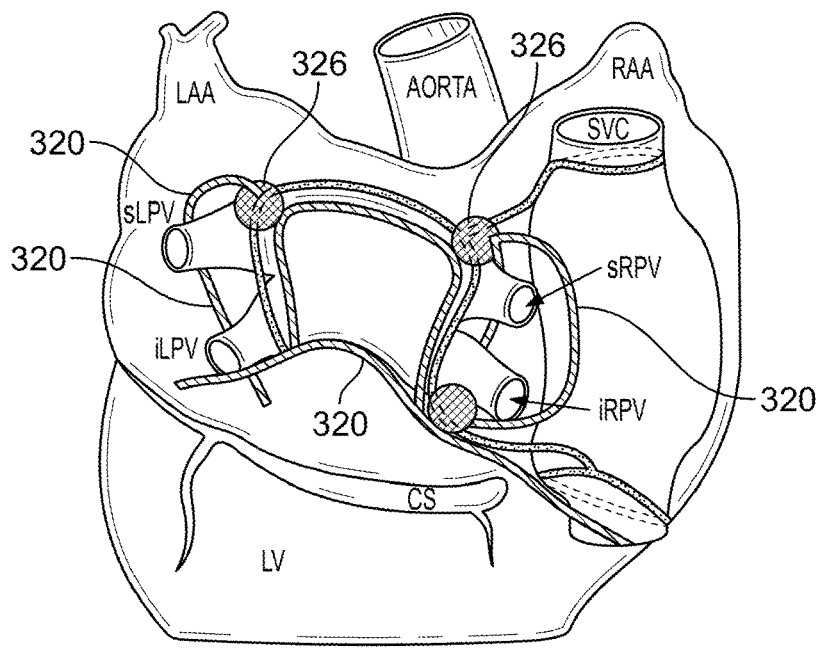

FIG. 3C shows one variation of a complete convergent coagulation pattern as the endocardial lesions 326 are created on the inner atrial surface. These lesions 326 intersect, join, and/or overlap epicardial lesions 320 to form the completed bi-atrial coagulation pattern. These endocardial lesions 326 are formed in areas on an endocardial surface that eliminate the need for dissecting pericardial reflections which attach the pericardium to the epicardial surface.

As discussed above, this technique allows creation of the desired coagulation pattern without dissection of any pericardial reflections. Instead, as shown in FIG. 3C, the epicardial coagulation occurring on the inner atrial surface creates lesions around the pericardial reflections since the lesions are on the inner surface of the heart. In addition, variations employing an abdominal entry approach for creating the epicardial lesions, allow a physician to create epicardial lesions without creating openings in the chest and without deflating the lungs. The abdominal entry access method also allows increased visualization around the areas of the pericardial reflections so rather than dissecting the reflections, a physician can use an epicardial coagulation device (or other device) to gently distort or push against the pericardial reflection to minimize the gap between lesion patterns.

In one variation of the method, the coagulation device placed on the outer surface of tissue can comprise one pole of an RF energy system where the second pole of that RF energy system is located on a second device that is on the inner surface of the tissue. Accordingly, during application of energy current flows between the two devices and through tissue to create a lesion. Another benefit of such a system is that the devices can be used to measure impedance of the tissue between the devices. In general, the impedance will increase as the devices are moved farther away and will decrease when the devices are closer together but on opposite sides of the tissue.

Figure 3D:
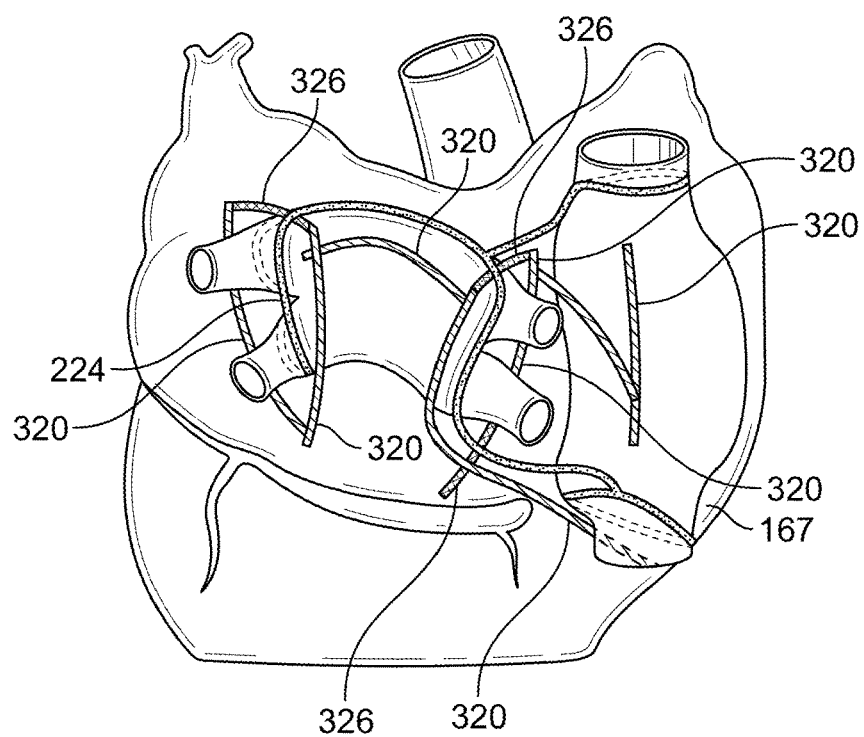

FIG. 3D illustrates another variation of a bi-atrial coagulation pattern. In this variation, an epicardial coagulation device creates epicardial lesions 320 around pericardial reflections 224 as shown. As with the previous technique, this procedure allows for creation of epicardial lesions 320 without dissection through the pericardial reflections. A commercially available ablation device is then used to create endocardial lesions 326 to connect gaps in the areas caused by the pericardial reflections on the epicardial surface.

Figure 3E:
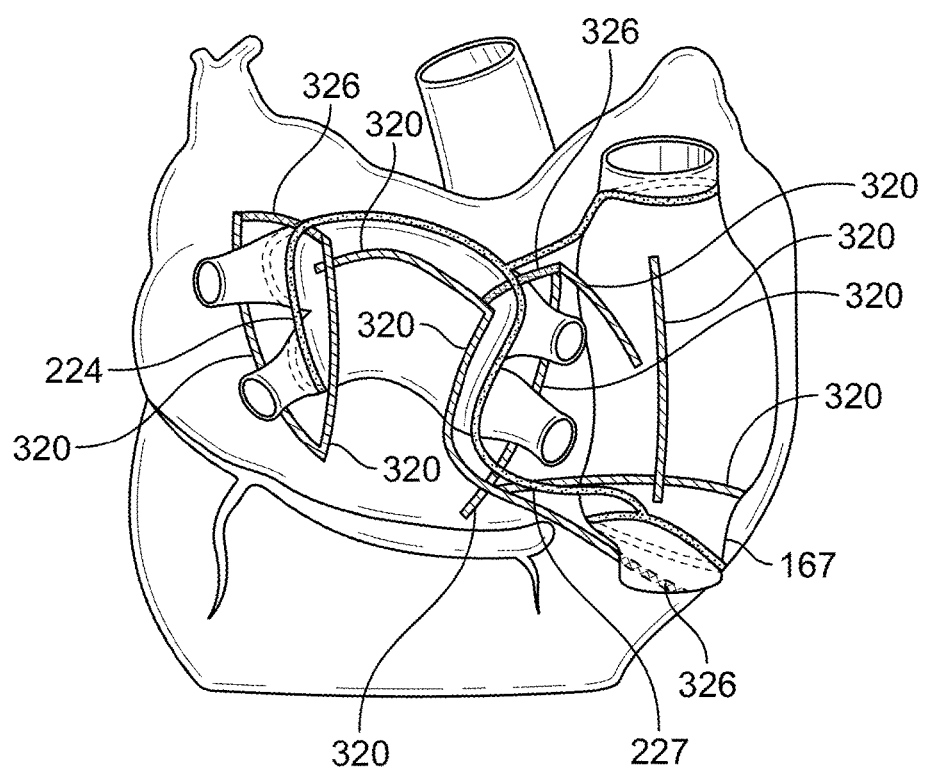

FIG. 3E illustrates another variation of a bi-atrial coagulation pattern. In this technique, an epicardial coagulation device creates epicardial lesions 320 around the pericardial reflections 224 as shown. However, the reflection located in front of the oblique sinus, as shown at 227, is dissected as well as the oblique sinus. Dissection at these locations is relatively easy because the location is in line with an access port when using a trans abdominal approach as disclosed below. Once the oblique sinus has been accessed, the right atrium lesions can be completed. Once again, an endocardial coagulation device creates endocardial lesions 326 across gaps that are at the top of the pulmonary veins. The endocardial coagulation device can also extend the endocardial lesion in front of the inferior vena cava.

The advantages of a bi-atrial technique versus a totally endocardial technique is that a bi-atrial pattern allows for a full lesion pattern, including left-atrium to right-atrium lesions where such lesions are only accessible from an epicardium. Moreover, the bi-atrial pattern allows the potential to coagulate the Ganglionated Plexi, which is only accessible from the epicardium. As noted above, the use of epicardial lesions minimizes the risk of coagulating from the endocardium outward. Also, the technique allows for preservation of atrial function since coagulation lines are along the pericardial reflections that tether the atrium and are relatively immobile.

The advantages of a convergent, combined epicardial and endocardial technique over an epicardial only techniques include: the ability to create a flutter lesion at the tricuspid isthmus, the ability to create lesions that connect the epicardial linear segments at the pericardial reflections to avoid the need to dissect the reflections resulting in decreased procedure time, and assuring lesion integrity and pulmonary vein isolation via endocardial mapping.

The methods and techniques described herein to create bi-atrial coagulation patterns can employ any traditional coagulation device for either the epicardial coagulation patterns or the endocardial coagulation patterns. The energy modalities can include those commonly used modalities, such as, but not limited to RF energy, a laser energy, infrared heating, chemical ablation, cryogenic ablation, microwave energy, and resistive heating. Examples of improved coagulation devices for creating lesions are disclosed in: U.S. Pat. No. 6,893,442 filed on Jun. 14, 2002 issued on May 17, 2005; U.S. Pat. No. 7,063,698 filed on Apr. 29, 2003 issued on Jun. 20, 2006; U.S. Pat. No. 7,410,487 filed on Mar. 30, 2005 issued on Aug. 12, 2008; U.S. Pat. No. 7,572,257 filed on Aug. 18, 2005 issued on Aug. 11, 2009; U.S. Patent Publication No.: US 2006-0200124 A1 filed on May 23, 2006; US 2006-0206113 A1 filed on May 12, 2006; US 2006-0235381 A1 filed on May 12, 2006; US 2007-0043351 A1 filed on Apr. 21, 2006; US-2007-0250058-A1 filed on Apr. 19, 2007; US-2008-0114354-A1 filed on Nov. 9, 2006; US-2008-0114355-A1 filed on Nov. 9, 2006; US-2008-0243119-A1 filed on Jun. 6, 2008; and US-2009-0254009-A1 filed on Jun. 16, 2009. The entirety of each of which is incorporated by reference herein.

Figure 4A:
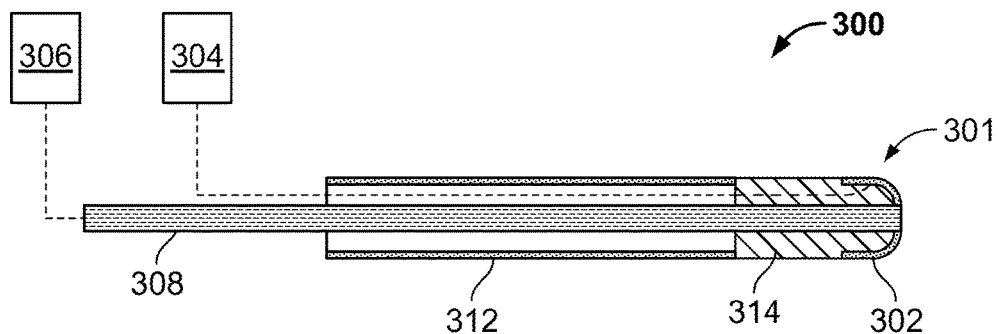
FIGS. 4A to 4C demonstrate various examples of devices for advancement into the heart.
Figure 4B:
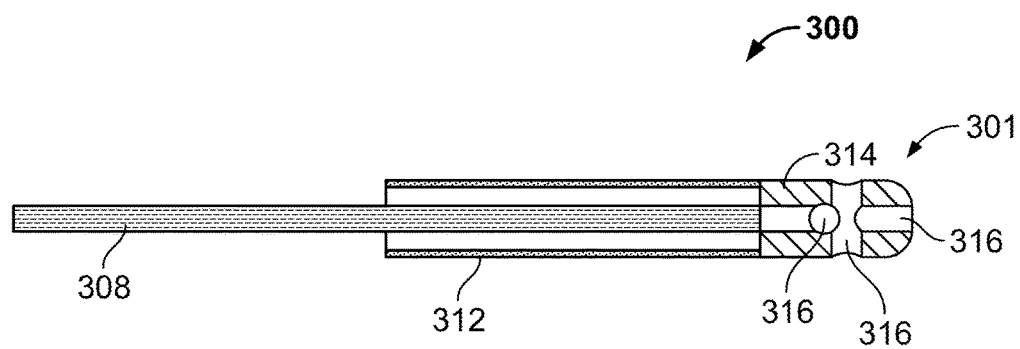
Figure 4C:
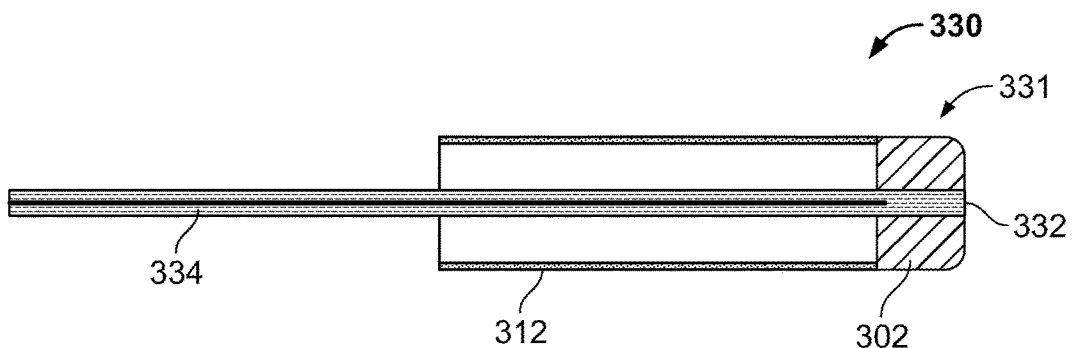

As discussed above, certain variations of the methods for creating a bi-atrial lesion pattern employ devices that permit location of the device through tissue. FIGS. 4A to 4C illustrate some exemplary devices that assist the physician in locating the coagulation device through tissue where the device includes a source of electromagnetic energy at a working end.

FIG. 4A illustrates a device where the source of electromagnetic energy comprises an illumination source. Accordingly, an illumination power supply 306 can be coupled to an illumination source 308 (such as an optical fiber) that extends through the body 312 of the device 300 and is exposed at or near a working end 301 of the device 300. In some variations, the illumination source 308 can comprise a light or light emitting diode positioned at the working end 301. Such a configuration could employ an external power supply or the power supply can be self-contained in the body 312 of the device 300. The illumination source 308 can optionally terminate in an illumination tip 314 that is configured to disperse the light or other energy about the circumference and front end of the working end 301. For example, the illumination tip 314 can comprise a transparent or translucent material such that the energy passes from the illumination source 308 into the illumination tip 314. In another variation, the illumination tip 314 can comprise a transparent or translucent balloon member. In yet another variation, the device 300 can comprise an intravascular catheter that is equipped with one or more electrodes 302 located at or near the working end 301 and coupled to a power supply 304. In such a case, the device 300 can comprise a traditional coagulation catheter with an illumination source coupled thereto or one in which the illumination source is constructed as part of the device.

FIG. 4B shows another variation of a device with an illumination source 308 coupled to an illumination tip 314. As noted above, the working end 301 may or may not have an electrode coupled thereto. In any case, the illustrated variation includes an illumination tip 314 having one or more openings or channels 316 for directing energy from the illumination source 308 in a desired pattern about the tip 314.

FIG. 4C illustrates another variation of a device 330 for creating bi-atrial lesion patterns. In this variation, the device 330 comprises an endocardial coagulation device 330 having one or more electrodes 302 located at a working end 331. The device 330 further includes one or more temperature detecting elements 332. As discussed below, as an endocardial catheter creates lesions, the temperature of the cardiac tissue rises. This change in temperature can be sensed with the temperature detecting element 332. The temperature detecting element can be of several different types known and used for measuring temperature of tissue or other temperature measurements. For example, the temperature detecting element can be a thermocouple an infrared temperature detecting device. Furthermore, the temperature detecting element can be a non-contact detecting element, such as an IR thermometer that is coupled to one or more of the access devices described below.

Clearly, any other temperature detecting device is within the scope of this disclosure. As an epicardial device coagulates tissue on an epicardial surface, the physician places the device 330 in contact with endocardial cardiac tissue to detect for a rise in temperature. As the temperature rises indicating that the device is properly placed adjacent to an epicardial lesion, the device 330 can be positioned so that the electrode 302 is energized to create an endocardial lesion at the site on the endocardial surface. In the illustrated example, the temperature-detecting element 332 can be coupled to a power supply (not shown) via the same conducting members 334 that couple the electrode 302 to a source of coagulation energy.

The source of electromagnetic energy described herein can comprise any form of electromagnetic energy that can be detected through tissue. Some examples of such energy include visible light, coherent light (e.g., a laser), ultraviolet light, magnetic energy, electrical energy, etc. Although the previous examples show the use of a visible light or laser, additional variations include electromagnetic energy that is not visible. Furthermore, as shown below, the electromagnetic energy source can communicate with a sensor that is placed on the opposite side of the tissue wall where the sensor is configured to measure the electromagnetic energy to determine the proximity between devices.

Figure 5A:
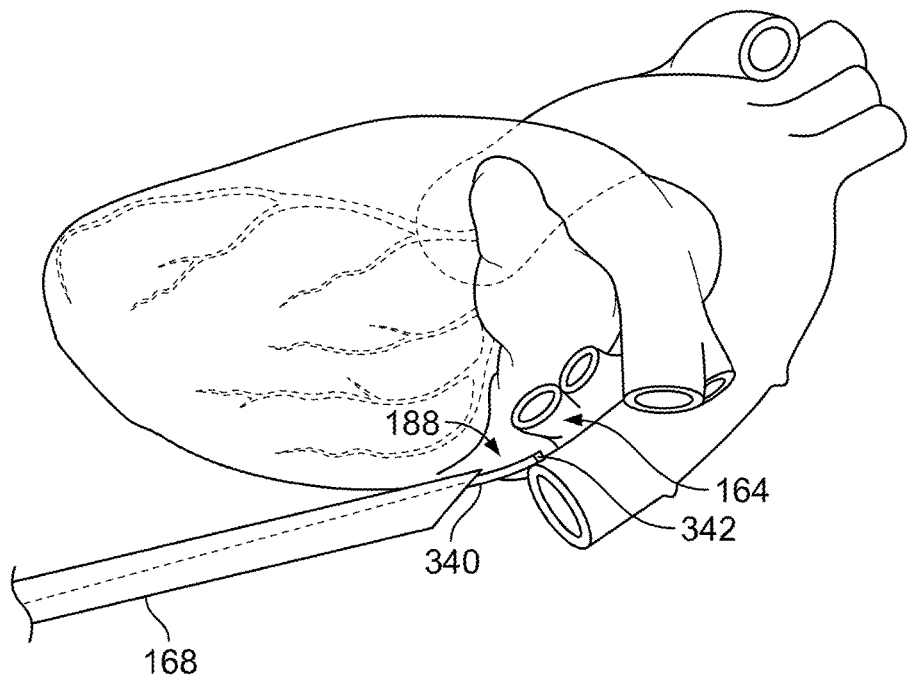
FIG. 5A shows an example of an access device providing a pathway to a posterior atrial surface with a sensor advanced through the access device.

For example, FIG. 5A illustrates an example of an access device 168 providing a pathway to a posterior atrial surface 188. The physician then advances a device 340 having a sensor 342 for detecting one or more paired sensors (or other sources of electromagnetic energy) on the opposite side of the atrial wall. The sensor 342 can be configured on a stand alone device or it can be incorporated into the epicardial coagulation devices as discussed herein.

Figure 5B:
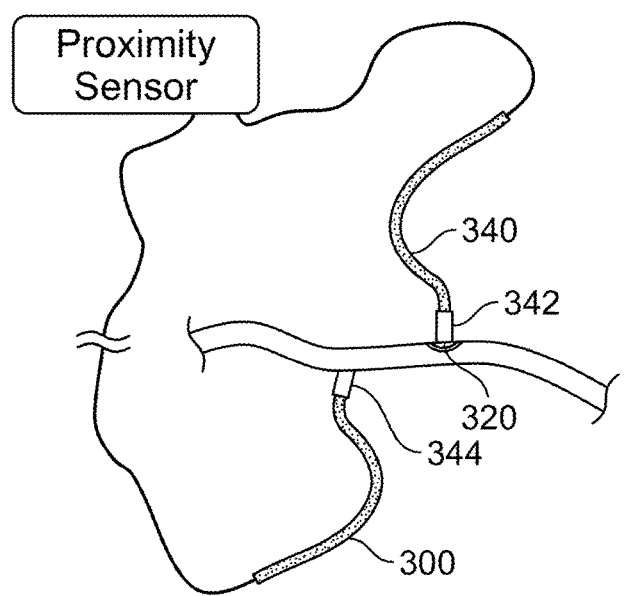
FIG. 5B provides a partial cross sectional view of the device of FIG. 5 as it is placed against tissue to locate a second sensor device within the heart.

FIG. 5B provides a partial cross sectional view of the device 340 of FIG. 5 as it is placed against tissue to locate a second sensor device 300. In practice, the physician can position the sensor 342 on or near the epicardial lesion 320. Then, the second sensor device 300 is moved on the opposing side of the tissue wall to detect the proximity of the catheter on the endocardial surface through non-visual means. By ensuring that the proximity of the two devices 300, 340 falls within a certain distance, the physician can increase the probability that lesions formed on each surface will connect to form the contiguous lesion. In some variation, the proximity sensor 342 and/or 344 can be calibrated such that the system will only alert to the proximity of the two devices when they are close enough to cause a connecting lesion. In one example, a physician can place the epicardial device 340 on the most distal portion of the epicardial lesion set. Then, the physician moves the endocardial device 300 to create the endocardial lesion. When the proximity sensor alarm is activated, the physician can be sure that the two lesions are connected Various technologies can be used to detect the proximity of the two devices. One method involves detecting the impedance between the epicardial and endocardial devices. Using this method, both devices are part of the same AC circuit and the impedance of the circuit can be measured. As the devices are moved toward each other, the impedance will drop. Once a pre-set threshold is reached (one that ensures a connecting lesion) an alarm sounds alerting the physician that the two devices will create a connecting lesion.

Another method of detecting proximity utilizes a magnetic detector. The epicardial device contains a micro magnetic field generator and detector. The endocardial catheter contains a ferrous element. When the ferrous element enters the magnetic field of the epicardial device, the magnetic field is disturbed and is detected by the epicardial device. The detector would be calibrated such that the system will only alert to the proximity of the two devices when they are close enough to cause a connecting lesion.

Another variation to create matching lesions for a bi-atrial coagulation pattern involves the use of an access device with a modified light source. The access device is inserted into a pericardial space to visualize lesions created from inside the heart. Several technologies are available that utilize specific wavelengths of light to enhance the visualization of tissue structures.

One such technology uses blue and green light to penetrate superficial tissue surfaces and visualize changes in the tissue (such as detecting the presence of blood vessels). Irradiating the tissue with these or other wavelengths of light can detect the presence or absence of ablated/coagulated tissue. The healthy tissue shows up as a different color from the damaged, ablated tissue. These imaging devices using narrow band imaging (provided by Olympus) can be combined with the access devices described herein to create joining lesions.

Another technology provided by Novadaq Technologies uses blue light to excite the naturally occurring flourophors in healthy tissue. Cells contain molecules, which become fluorescent when excited by ultraviolet or near ultraviolet/visible radiation of suitable wavelength. This occurrence is known as autoflorescence. When tissue is damaged, it exhibits reduced autoflorescence. By utilizing this phenomenon, tissue that has been ablated can be distinguished from healthy tissue.

Another similar technology utilizes a narrow band of light (such as a laser) to excite a fluorescing non-toxic dye such as indocyanine green (ICG). The use of a dye allows the detection of a lesion because the ablated tissue will have little to no perfusion of blood through it. Therefore the dye will not appear within the boundaries of the lesion, but will appear is all other tissue. The tissue surrounding tissue will fluoresce while the lesion itself will not.

As discussed above, creation of a bi-atrial lesion can be performed with any conventional access to the thoracic cavity. Furthermore, the methods and devices described herein may be used in conjunction with, or as an alternative to the conventional approaches described herein. In general, surgical approaches and procedures described herein that rely on entry through the diaphragm of a patient to access a posterior region of that patient are referred to as "Diaphragm Entry for Posterior Access" or simply "DEPA"). The DEPA procedure may also be referred as VAPS (Video-Assisted Pericardiac Surgery) or TAPS (Trans-Abdominal Pericardiac Surgery).

Methods allowing for access to the posterior surface of the heart can improve a physician's ability to observe the atrial surface. Such a technique, though optional, can assist the physician in creating a bi-atrial lesion. Examples of methods and devices for creating such access paths into the body are disclosed in U.S. Patent Publication Nos.: US-2007-0083082-A1 filed on Apr. 21, 2006; US-2008-0114342-A1 filed on Nov. 9, 2006; US-2008-0114288-A1 filed on Nov. 9, 2006; US-2007-0083225-A1 filed on Apr. 21, 2006; US-2007-0249991-A1 filed on Apr. 19, 2007; US-2009-0312783-A1 filed on Jul. 16, 2008; and US-2009-0270676-A1 filed on Apr. 23, 2008. The entirety of each of which is incorporated by reference herein.

Figure 6A:
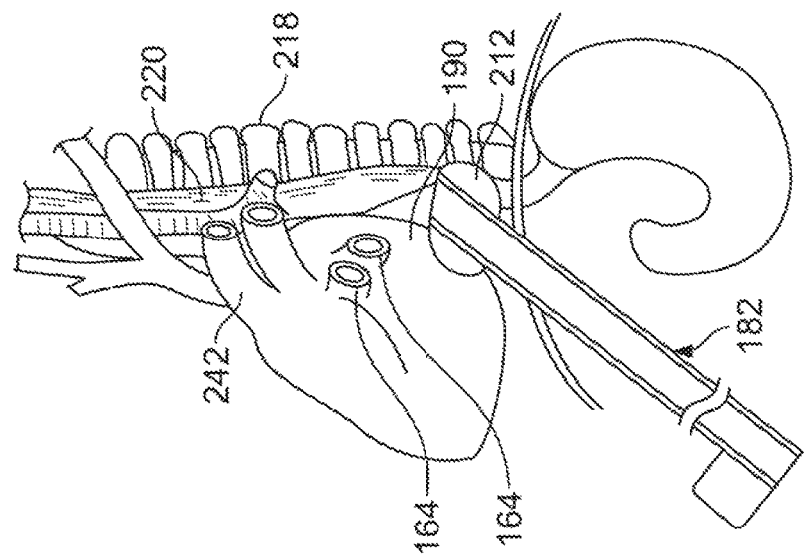
FIGS. 6A and 6B show a partial side view of the thoracic cavity and demonstrates an example of insertion of an access device into the abdominal space and ultimately into the thoracic cavity.

FIG. 6A shows an example of placement of access devices 182 (also referred to as a separator or an elevator herein) useful for accessing a posterior surface of the heart. An access device 182 is inserted through, at least a first, an abdominal, incision 168. The device is then advanced through the diaphragm 170 and pericardium (not shown) and placed adjacent or between organs for creation of a temporary cavity. The procedure may include the use of one or more optional ports 106. The ports 106 in this variation are placed to allow access to the right side of the thoracic cavity. When placing right side access ports, the ports may be placed along any region of the body to provide access to the right side of the thoracic cavity.

When used, the ports 106 provide a surgeon with a second location to manipulate devices within the thoracic cavity. The access device 182 allows for manipulation/visualization of such devices in a posterior region of the thoracic cavity while the ports 106 allow for manipulation/visualization in the anterior region of the thoracic cavity. One such benefit of having dual access is that a guide wire or catheter can be inserted via the access device 182 and then navigated through and around organs towards the anterior region of the organ. In one example, use of this dual access allows for creation of a variety of coagulation regions on the pericardial tissue. Accordingly, the surgeon can dissect less (or no) pulmonary vein reflections and is able to directly visualize and control posterior left atrial lesions without creating left sided ports or incisions. The benefits of eliminating the left sided ports include decreased trauma to the patient and increased recovery time since the surgeon can allow the left lung to remain inflated.

Figure 6B:
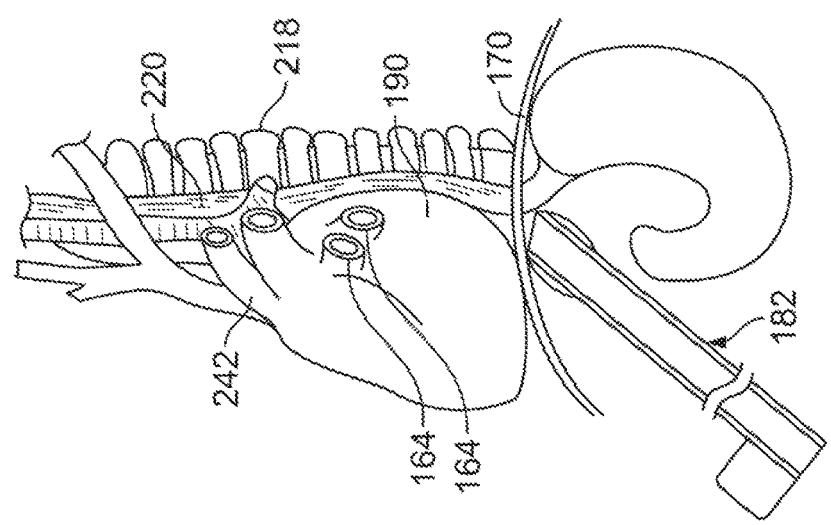

FIGS. 6A and 6B illustrate partial cross sectional views of a patient's thoracic cavity and abdomen to demonstrate a general principle of a DEPA procedure. For the sake of clarity, certain organs are not shown in the figures. FIG. 1D illustrates the DEPA procedure after the patient is prepared (as discussed herein) and after the DEPA incision is made within the abdomen. As shown, the DEPA incision allows entry of an access device 182 within the abdominal space and adjacent to a diaphragm 170. An incision in the diaphragm may be made using cutting features incorporated in the access device 182, a tool advanced through the access device 182, or via another tool advanced through another abdominal port or a thoracostomy port.

FIG. 6B shows an example of an access device 182 as it creates a temporary space within the thoracic cavity by separating the posterior ventricular surface 190 of the heart from the spine 218 and esophagus 220. As discussed below, the methods described herein contemplate creation of a temporary cavity about any organ such that the access device separates one or more additional organs from the desired surgical space. FIG. 6B shows the expansion of expandable members 212 (e.g., as discussed below: inflatable bladders, expandable strands, etc.) to separate adjacent tissues and form a temporary cavity. The access device can be used to separate the esophagus from surrounding tissue to aid with an esophogectomy procedure. In the variation shown, the access device 182 creates the temporary cavity at a posterior surface of the heart without the use of expandable members. As described below, the temporary cavity may be formed where needed including the various other organs and/or tissue surfaces within the body. This temporary cavity permits improved surgical and visual access to various tissue surfaces without the use of complex equipment. In general, the improved access provides the surgeon the ability to perform additional procedures that would otherwise be difficult or impossible.

It may be advantageous to distort the surface of the atrium when creating lesion patterns as described herein. Currently, it is difficult to reach some areas of the atrium from an intravenous catheter due to the tortuous path the catheter must take to reach the endocardial surface. Distorting the atrial tissue with an atrial manipulator as described herein or in the above reference published applications can assist the physician when attempting to engage a coagulation device with hard to reach surfaces.

One embodiment of this atrial manipulator is a shaped probe that is inserted through an access device or cannula 182 into the pericardial space around the atrium. The shape of the probe allows for distortion of the atrial wall in such a way as to cause the endocardial surface to bulge into the path of an endocardial coagulation device. See FIG. 8. The shape of the probe could be designed such that by altering the location of the probe from the access device 182, different portions of the atrium would be contacted and manipulated. For example, as shown in FIG. 7A, the scope 184 could represent (or be used as) an atrial manipulator to distort the atrial wall.

Alternately, the access device 182 itself could be designed to alter the shape of the atrial wall. In one embodiment, a shape present on the exterior surface of the cannula would cause the atrium to move into the path of an endocardiac catheter.

FIGS. 7A to 7B illustrate side-sectional side views of the access device 182 when inserted through an opening in the diaphragm 240. As shown, the access device 182 enters the patient through an abdominal incision 168 below the diaphragm 170. The device 182 then advances through diaphragm (e.g., via an incision 240) and the pericardium (not shown) to access the posterior organ surfaces. As noted below, the access device 182 defines a tube 210 having at least one working channel 211 through which the instruments can be inserted and manipulated. A scope 184 (hereafter a "DEPA scope") can be used to visualize a substantial portion of the posterior heart (posterior atrium 188 and posterior ventricle 190) and/or other organs/tissue. Typically, the scope 184 transmits an image to an external monitor 181. Once the surgeon positions the device 182, expandable members 212 on the device may be actuated to create a temporary cavity within the body. In this variation, the expandable members 212 comprise inflatable bladders or balloons that expose a posterior atrial surface 188 and a posterior ventricular surface 190 of the heart.

As shown in FIG. 7A, entry into the thoracic cavity via the diaphragm allows the access device 182 to form a smooth transition/angle from the access site into the patient to the posterior surface of the organs in the thoracic cavity (e.g., heart, lungs, esophagus, etc.). The traditional approaches mentioned above require multiple steep angles that require excessive manipulation of devices and do not offer visualization without complex equipment. Such equipment introduces significant difficulty in manipulation and viewing perspective. The angle of entry provided by the access device 182 via the diaphragm 170 allows use of a straight scope, having a viewing angle between 0 and 60 degrees, to visualize the posterior surface of the organs. Flexible scopes may be used but are not necessary because of the smooth transition and shallow angle of insertion from the skin puncture site to the diaphragm incision adjacent the posterior heart surface.

Yet another benefit provided by the diaphragm entry method is that a surgeon may manipulate instruments within the thoracic cavity in an easier and more controllable manner. For example, use of conventional techniques requires that a surgeon operate with a device having a near 90 degrees bend. Manipulation of such a device is difficult since pushing down directs the device away from tissue and the organs within the thoracic cavity interfere with the device when pulled upward. Use of relatively complex steerable equipment introduces complexity as well as reduces the surgeon's tactile feedback.

FIG. 7B illustrates the access device 182 positioned in the thoracic cavity as the surgeon manipulates a surgical tool 124 in the thoracic cavity. As shown, the DEPA scope 184 allows posterior visualization of the surgical site. In many cases it is important to keep the visual field clear from fluids. Accordingly, the access device 182 may have an aspiration tube 252 or separate aspiration lumen to draw fluids from the surgical site.

Figure 7C:
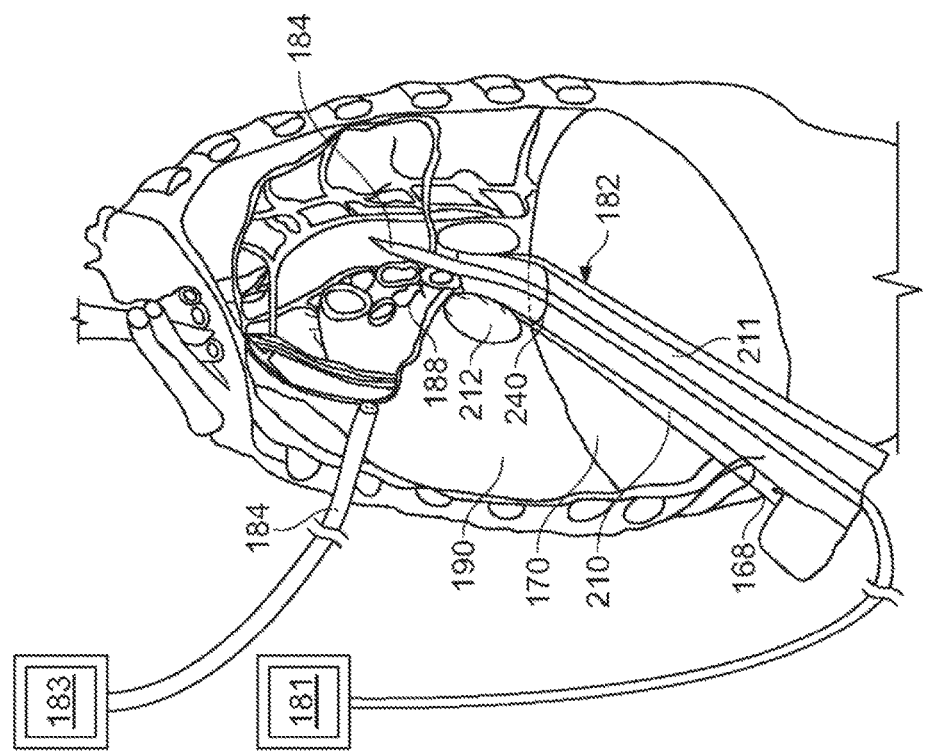

FIG. 7C illustrates another variation where the surgeon positions the access device 182 in the thoracic cavity. However, in this variation, the surgeon may also use a second scope 184 advanced in a conventional manner as discussed above. The purpose of the second scope 184 is to view the anterior surface of the organs. This arrangement allows visualization of the anterior and posterior surfaces of the organ. Accordingly, as a surgeon performs a procedure on an anterior or posterior surface, if the surgeon breaks through to the opposite surface (i.e., the posterior or anterior surface) use of the two scopes 182 and 184 improves visualization. In one example, the DEPA scope may be used merely for posterior visualization during a video assisted thoracostomy procedure. Again, as noted herein, additional ports/trocars 106 can be placed to provide direct access to the thoracic cavity for manipulation of the treatment or other devices to ensure accurate creation of coagulation patterns across the various organs.

Figure 8A:
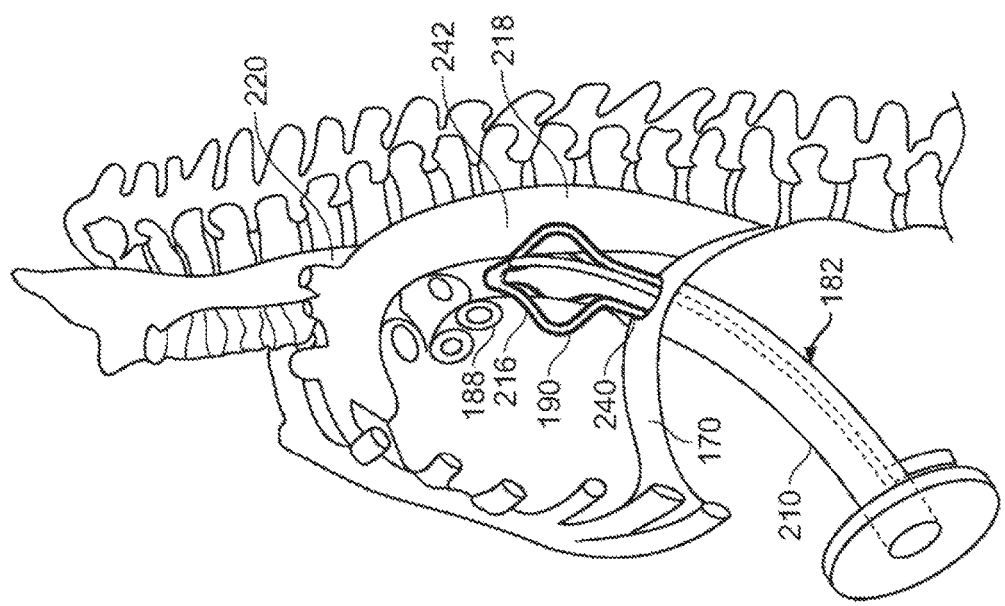

FIG. 8A to 8B, illustrate another variation of an access device 182. As shown in FIG. 8A, the device 182 includes expandable member 216 in the form of expandable stabilizer strands 216. Alternatively, as described above, the expandable member may comprise a set of balloons or bladders. Once the surgeon positions the access 182 device in place, the expandable members 216 actuate to separate the organs and define a temporary cavity. Once the surgeon completes the procedure, the expandable member 216 collapses, thereby causing closure of the temporary cavity. In this variation, the expandable members 216 separate the esophagus 220 from the descending aorta 242 while also stabilizing both organs. This action serves to protect these anatomic structures while defining the temporary cavity.

FIG. 8B illustrates placement of an ablation device 2 (e.g., as those described herein) through the working channel(s) 211 of the device 182. As shown, the temporary cavity permits visualization of a posterior surface of the organ (in this case the heart). This action allows the surgeon to ablate or treat the posterior surfaces of the heart. For example, the surgeon may treat the pulmonary veins located on the posterior surfaces on the heart without having to dissect the veins from the heart. As noted above, to keep the visual field clear from fluids, the access device 182 may have an aspiration tube or separate aspiration lumen to draw fluids from the surgical site.

Without posterior access, a surgeon would have to dissect the veins away from the heart's surface and then attempt to perform the procedure. Even in such a case, without posterior visualization, the surgeon is forced to treat portions of the veins blindly. On the other hand, a surgeon using a scope-type device (such as a DEPA scope 184 as described above), as shown in FIG. 8C, can directly visualize the posterior surfaces of the heart and veins during the treatment.

Another technique made possible through use of the access device 182 and diaphragm entry is that the surgeon can create a lesion on each side of a pulmonary vein (and in fact, an entire lesion pattern capable of treating atrial fibrillation) without having to dissect the pulmonary veins from the pulmonary artery, superior vena cava, or pericardium. The access device 182, as shown in FIG. 8C, allows the surgeon to reach the inferior surface of the pulmonary veins 189 located on the posterior atrial surface 188. Therefore, the surgeon has access along each side of the left pulmonary veins, and each side of the right pulmonary veins. Furthermore, the surgeon may apply additional lesions to the posterior surface of the heart with minimal or no dissection of the pulmonary veins.

FIG. 8C also shows another variation of the DEPA methods, where an access device 182 separates adjacent tissue to create a temporary cavity. The surgeon then may advance treatment devices 2 and visualization devices (e.g., an endoscope 184) to the temporary cavity but external to the access device 182. As shown, the treatment device 2 permits creation of a lesion on the posterior surface of the heart and on the pulmonary veins. In this variation, the access device 182 uses stabilizer strands 216; however, any variation of device may be used.

Figure 8D:
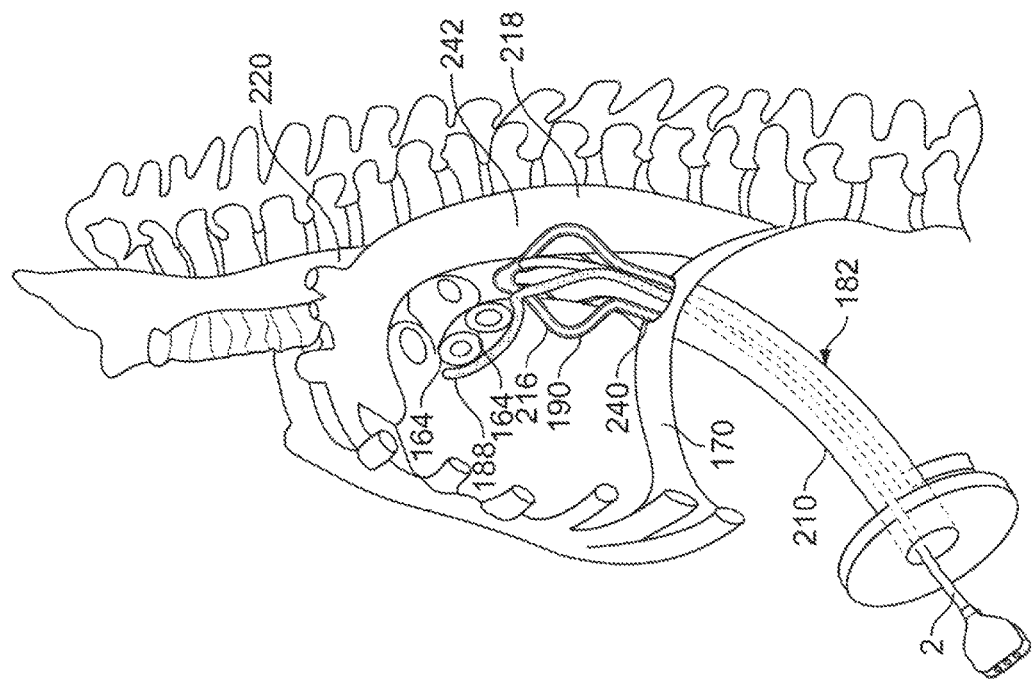
FIGS. 8D to 8F show side views of a thorax to illustrate accessing a posterior atrial surface around pulmonary veins without having to dissect tissue around the pulmonary veins.
Figure 8E:
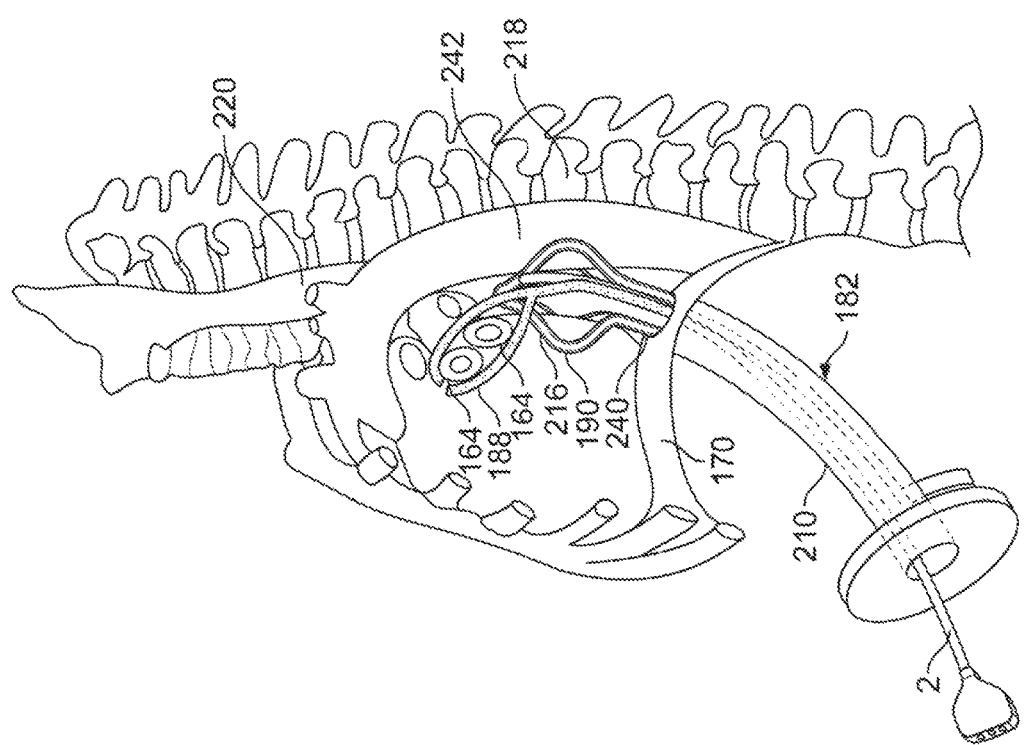
Figure 8F:
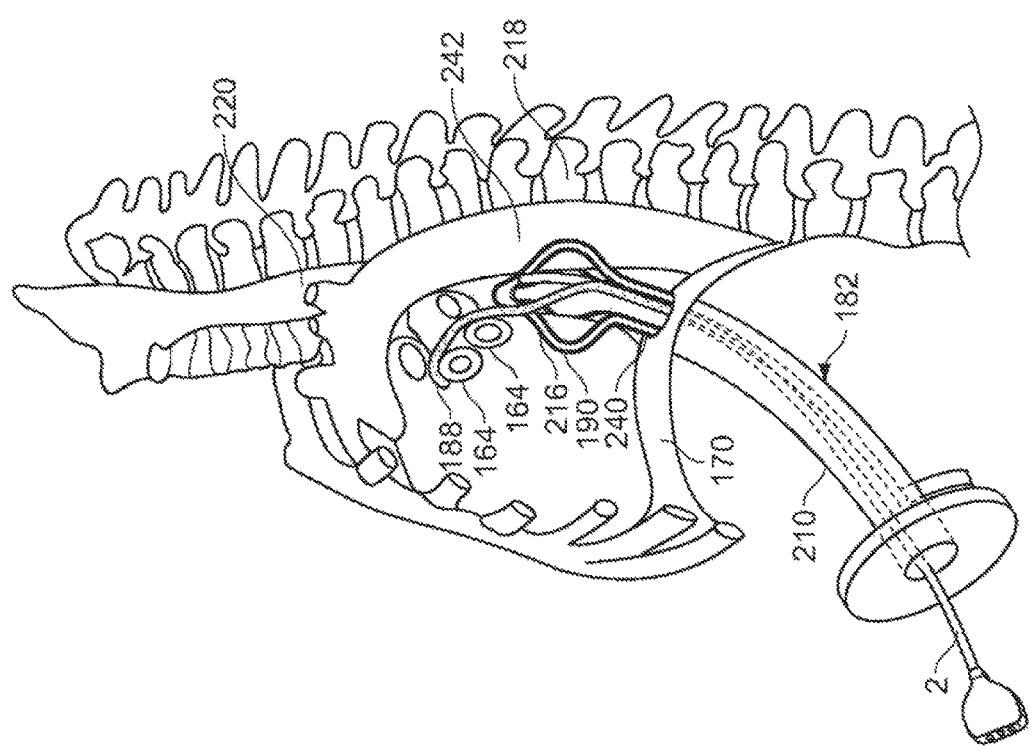

FIGS. 8D to 8F illustrate another variation of a DEPA method that is made possible because of access to the posterior region of the heart. As noted above, conventional approaches intending to apply coagulation devices to a posterior surface of the heart requires dissection of tissue to access the posterior surface. Typically, when the surgeon intends to create a coagulation line around the atrial surface adjacent to the pulmonary vein, the coagulation device is inserted around the pulmonary vein that is dissected from cardiac tissue. Because the DEPA method provides direct access to the posterior surface of the heart, the pulmonary veins and surrounding atrial surface are directly visible and accessible without dissection of tissue. As shown in FIG. 3D, a treatment device 2 can access the posterior atrial surface 188, in this case around the pulmonary veins 164, without having to dissect tissue.

FIG. 8D, illustrates a variation of a treatment device 2 that has two opposing s-type electrodes. This device allows formation of a coagulation line around the pulmonary veins. FIGS. 8E and 8F illustrate treatment devices 2 using a single c-type electrode configuration to form coagulation lines on the atrial surface 188 around each side of the pulmonary veins 164. The use of the access device 182 and methods for posterior access allow for the creation of any number of coagulation patterns. The use of additional ports for thoracoscopic access is optional. For example, a surgeon can place the access device through the diaphragm entry method, and create any coagulation lesion patterns (or even a single or few coagulation lines) where desired using any conventional device. For instance, a surgeon could perform a coagulation procedure that isolates the pulmonary veins by advancing a clamp-type coagulation device through the access device such that electrodes of the clamp jaws are oriented on two sides of the left or right pulmonary veins, preferably along the antrum that connects the superior and inferior branches of the pulmonary veins to the left atrium. Once the jaws are actuated, the clamp-type coagulation device compresses the pulmonary veins (preferably along the antrum or at the orifice to the left atrium) between the jaws allowing the creation of a lesion that completely isolates the pulmonary veins from the rest of the atrium. The same action may be subsequently used to isolate the opposing (right or left) pulmonary veins. Accordingly, isolation of the pulmonary veins can be performed via diaphragm access to the thoracic cavity without creating any additional openings in the chest.

Direct visualization of the posterior heart surface (or the esophagus or the lung) provides the surgeon with confidence when manipulating instruments along the cavity between the heart and lungs, and the spine and esophagus. An additional benefit of the DEPA process and associated devices is the ease of deployment due to the direct line to the posterior surface of the anatomy and the rapid healing post-procedure due to the absence of or limited deflation or other manipulation of the lungs when manipulating instruments along the posterior heart, the esophagus, or the posterior lung surfaces. The small incisions used to access the posterior heart surface during the DEPA process accelerates the healing process and reduces the visible scar.

As noted above, the methods and procedures described herein contemplates the use of any surgical device that may be advanced through the access device to perform any procedure that benefits from or requires posterior visualization of organs as described herein. The integrated vacuum coagulation probe embodiments in the patents and applications referenced above provide examples of devices that allow intimate contact specifically between a soft tissue surface and the energy portion of the device. In those example, the electrode(s) used to transmit energy (radiofrequency or ultrasonic) is capable of heating the soft tissue until achieving irreversible injury making the soft tissue non-viable and unable to propagate electrical impulses, mutate, or reproduce. These integrated vacuum coagulation probe embodiments may be utilized during the DEPA process of the invention to coagulate soft tissue capable of treating atrial fibrillation, ventricular tachycardia or other arrhythmia substrate, or eliminating cancer in lung, or other soft thoracic tissue by destroying target cells.

In addition, these integrated vacuum coagulation devices may be used to heat soft tissue along the posterior heart surface resulting in heat-induced contraction of collagen in such tissue thereby resulting shrinking of said soft tissue. For example, heating the mitral valve annulus along the posterior atrio-ventricular groove may induce shrinking of the annulus thereby correcting mitral valve regurgitation. However, it is understood that the invention is not limited to the above described vacuum coagulation probes. Instead, any number of coagulation, ablation, or surgical devices may be used as required.

The DEPA process and associated devices provide direct access to the posterior surface of the heart or lungs, or the esophagus, ascending or descending aorta, pulmonary artery, or other soft tissue structure, and enable manipulation of tissue structures to complete the desired surgical procedure. For example, the DEPA process facilitates accessing and visualizing the posterior left and right atria when creating lesions of structurally strong but electrically non-viable tissue along the atria to treat atrial fibrillation, atrial flutter, or other supraventricular tachycardia, or along the ventricles to treat ventricular tachycardia. In addition, such devices and methods could simplify and improve other soft tissue coagulation procedures by ensuring direct visualization while precisely and effectively heating a region of soft tissue. For example, ablation of cancer tissue in the lung or other anatomic structure is improved by the DEPA process and device embodiments of the invention. Similarly, the DEPA enables instrument manipulation and visualization for other cardiac (or non-cardiac) procedures that required accessing the posterior heart (or posterior lung or other anatomy between the posterior heart/lungs and the spine). For example, DEPA process will facilitate mitral valve compression procedures that involve placing patches or other compressive mechanism along the posterior mitral valve annulus adjacent to the posterior commisseur that is commonly associated with deformation due to ischemic injury or other cause of mitral regurgitation.

The DEPA process and device embodiments also enable reliable and controlled coagulation of soft tissue during less invasive procedures. Electrode(s) or antennas transmit energy (radiofrequency, direct current, ultrasonic, laser, infrared, or microwave) into tissue to cause the targeted soft tissue to heat thereby causing cellular responses that result in inhibiting conduction of electrical stimuli through the tissue cells but maintaining structural strength of the soft tissue. Alternatively, a cryogenic mechanism may be used to cool tissue below the isotherm of irreversible conduction block thereby rendering the tissue non-functional but structurally viable.

DEPA process embodiments and associated devices of the invention as applied to treating atrial fibrillation are described as an augmentation to other surgical access or as a stand alone surgical access. The DEPA process and associated devices of the invention may be used to augment other surgical access (e.g. thoracostomy, subxyphoid, mini-sternotomy, etc.) or may replace all other surgical access and provide the sole access for performing the surgical procedure.

FIGS. 7A to 7C show an example of a access devices 182 for creating a temporary cavity within the body. FIGS. 7A to 7C show, respectively, a top view, a side-sectional view, and an end view of an alternative access device 182. Generally, the device elevates organs and separates adjacent organs or tissue surfaces to create a surgical area within the body via creation of a temporary cavity. In the variation of FIGS. 7A to 7C, the device 182 incorporates two expandable members 212. As described herein, the device 182 may include any number of expandable members 212. However, regardless of the number used, the expandable members 212 expand about the elongate member 210 (also referred to as a guide tube) to separate and elevate organs to create the temporary cavity.

In the variation shown in FIG. 9A, the expandable members comprise two balloon bladders 212 (or a single balloon can be secured to the top and bottom of the elongate member 212 to define two bladders). The balloons 212 are oriented along the two opposing sides of the elongate member 210. When the balloons 212 inflate, as shown in FIGS. 9A and 9B, they form a pillow-type support that fits around the spine and esophagus on one side and the heart on the other side. In this manner, the balloons 212 serve not only to separate the organs, but also to stabilize them. It should be noted that the separation of the balloons on the elongate member does not need to be symmetric, as shown in FIG. 9C but may be different depending upon the particular application. For example, a shorter balloon can be used along the side of the device 182 that contacts the heart and a longer balloon can be used on the side of the device 182 that contacts the spine and esophagus, or vice-versa, depending on the patient anatomy. The balloons may be fabricated from silicone, urethane, polyester, PET, polyurethane, nylon, PEBAX, or other polymer capable of enlarging in response to being exposed to an inflation media. The guide tube 210 can be fabricated from any polymer and preferably has enough rigidity to provide column strength needed when inserting the access device into the space between organs (e.g., the heart and the spine). For example, the guide tube can be fabricated from polyurethane, PTFE, FEP, polyester, or other material that can be extruded or molded into the desired shape.

In variations of the access device 182, the expandable members (e.g., balloons 212) expand in a non-uniform manner about the elongate member 210. For example, as shown in FIG. 9C, the balloon 212 expand away from the sides of the elongate member 210 more than they expand away from the top and bottom of the elongate member 210. This particular configuration permits creation of the temporary cavity without moving the organs to far from the opening 186 or slot 187 of the elongate member 210. Although variations of the access device 182 include expandable members that expand non-uniformly about the elongate member 210, the device includes variations where the expandable member expands in a uniform manner as well.

As shown in FIG. 9B, the elongate member 210 includes at least one inflation lumen 214 that is fluidly coupled to the interior of one or both balloons 212. Depending on the application, each balloon 212 may have an individual inflation lumen 214 to provide more control over inflation of the balloons and separation of the organs. The balloons may be inflated using saline, $CO_2$, or other biocompatible fluid. The inflation lumens may be routed to the proximal end of the device including through ports in the handle. As discussed herein, the individual balloons may be inflated to different pressures and/or volumes such that one balloon provides more separation than the other. For example, when used against the heart, this mechanism causes the heart to rotate in one direction or the other providing a mode of manipulating the heart within the thoracic cavity. For example, this manipulation allows instruments to better access the lateral surfaces of the heart, and/or even the anterior surface of the heart.

FIG. 9C illustrates the elongate member 210 including one or more visualization elements 246. The visualization element may be an optic fiber, a CCD camera, a light source, etc. The optic fiber could be used to transmit light and illuminate the cavity defined by the access device 182. Alternatively, or in combination, the access device 182 may incorporate near-field infrared transducers to identify blood vessels (veins and arteries) during use. By incorporating such near-field infrared transducers, the surgeon can identify blood vessels (e.g. the pulmonary veins, coronary sinus, esophageal vessels, or other small vessels while getting to the heart or separating the esophagus) and avoid them while dissecting or localizing them. Such near-field infrared technology can visualize vessels 2 mm under the surface of tissue.

As shown in FIGS. 9A to 9C, the device 182 includes a working channel 211 that permits delivery of surgical tools and/or scopes to the temporary cavity. This allows for creation of a surgical field at the temporary cavity. The working channel 211 terminates at the opening 186 at the distal end of the elongate member 210. Although FIGS. 9A to 9C illustrate the opening 211 at a front face of the device 182, the opening 211 may be located at an end of the device 182 on a side as shown below.

The device 182 may also include a slot-type opening 187 on one or more sides of the elongate member 210. The slot 187 permits access to a larger portion of the organ within the temporary cavity. As shown, the ends of the balloons 212 extend beyond the slot 187 improving the ability of the device to form the temporary cavity. When the device is used against the heart, the slot provides access to the posterior heart surface located within the contact region between the access device and the heart. Without the slot 187, the access is only beyond the opening 186 of the elongate member 210.

As shown in FIGS. 9A to 9C, variations of the access device 182 include elongate members 210 having non-circular cross sections (e.g., oval as shown). The non-circular cross section of the working channel 211 provides the ability to place multiple instruments through the access device 182. To further increase the ability of the device 182 to handle multiple tools, devices 182 of the present invention may be used with scopes having camera connections that are oriented at an angle (e.g. anywhere up to 90 degrees) from the scope shaft so the handles will not interfere with the scope camera.

In the examples shown in FIGS. 9A and 9B, a planar surface 245 on one side of the device 182 permits an increased surface area contact between the device and tissue when creating the temporary cavity. This increased surface contact provides additional stability of the device 182 when in use. Although the expandable members 212 are shown to be placed on sides of the device 182 adjacent to the planar surface 245, additional variations of the device include expandable members on any surface/side of the device 182.

As shown, a proximal end or proximal portion of the access device 182 is adapted to allow manipulation of the access device from outside of the body. FIG. 9A illustrates proximal handles 256 that allow manipulation of the access device 182 and also prevents pushing the proximal end of the elongate member 210 or access device 182 completely into the patient.

As shown in FIGS. 9B and 9C, a malleable or shapeable support 244 may be incorporated into the elongate member 210 to allow shaping the member into a desired configuration. The shape is selected to improve the ability of the device to direct the scope and instruments towards the desired site of a temporary cavity (e.g., posterior region of the heart, or other anatomic structure). The support 244 may be placed in a support lumen such that the support 244 is slidable within the support lumen of the elongate member 210. Alternatively, or in combination, the elongate member 210 may be fabricated from a shapeable material. Accordingly, the elongate member 210 could be shaped to a desired profile.

FIG. 9C also illustrates the access device 182 as having an optional suction or aspiration lumen 262. Because the device is suited for creation of a temporary cavity to perform a surgical procedure under direct visualization, it will be important to keep the scope or visual element clear from bodily or other fluids. Accordingly, a suction device may be advanced through the working channel. Alternatively or in combination, a suction or aspiration lumen 262 may be placed within the elongate member 210.

Figure 9D:
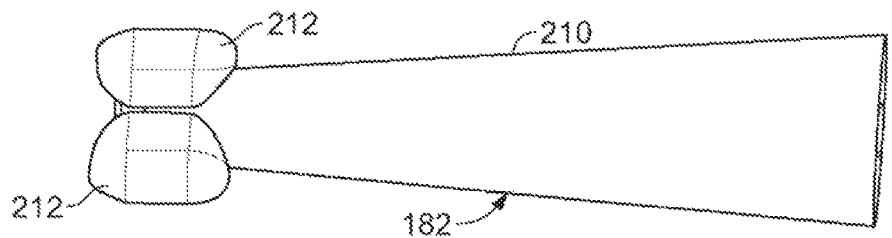
FIGS. 9D to 9E show another variation of an access device having a tapered elongate member.
Figure 9E:
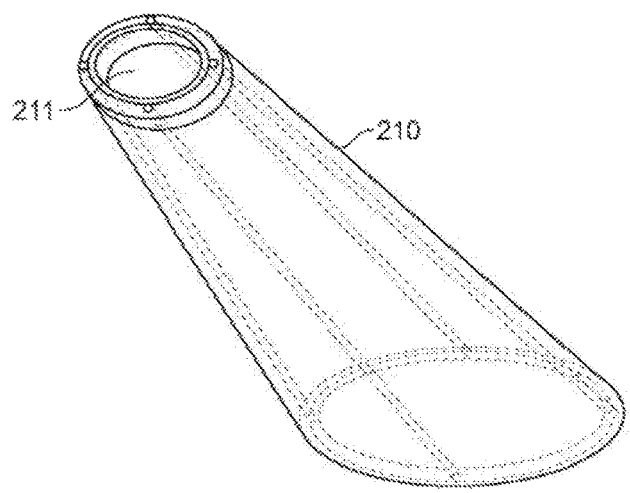

FIGS. 9D to 9E illustrate another variation of an access device 182. In this variation, the elongate member 210 is tapered from the proximal end the distal end. This tapering configuration allows the elongate member 210 itself to separate tissue as the device 182 advances to a target site. FIG. 9E illustrates a perspective profile of the tapered elongate member 210 (showing the various inflation and/or aspiration lumens). Again, the cross-sectional profile of the working channel 211 may be any geometric shape. However, shapes in which working channel width is not equal to the working channel height may be preferred (e.g., rectangular, oval, trapezoidal, etc.). FIG. 9C also demonstrates a variation of a device 182 where the expandable members 212 surround the distal end of the elongate member 210. This variation creates a space between the elongate member 210 and the organ.

Figure 9F:
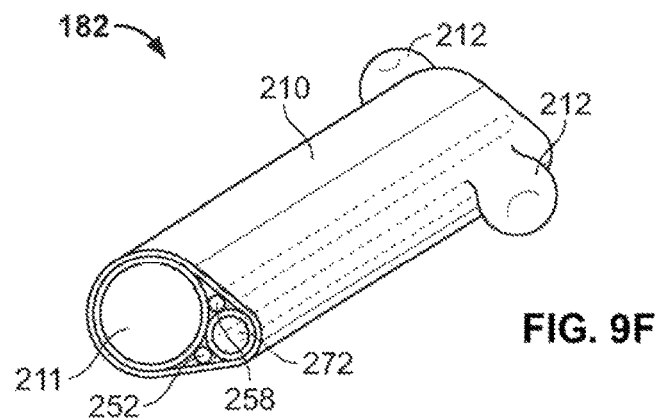
FIGS. 9F to 9I show variations of an access device having a working channel and a second working lumen.

FIGS. 9F to 9I illustrate additional variations of access devices 182. As shown in FIG. 9F, the access device 182 may include an additional working lumen 272 within the elongate member 210. The additional working lumen 272 in this variation is separate from the working channel 211 and provides an access channel that permits the ability to leave a device at the temporary cavity while advancing and/or removing other devices without causing undue interference between devices. For example, the additional working lumen 272 may be used to advance a scope-type device to the temporary cavity. In this manner, the scope-type device may be left in the working lumen 272 while other devices are inserted and manipulated in the working channel 211. This reduces the chance that the scope is disturbed.

Figure 9G:
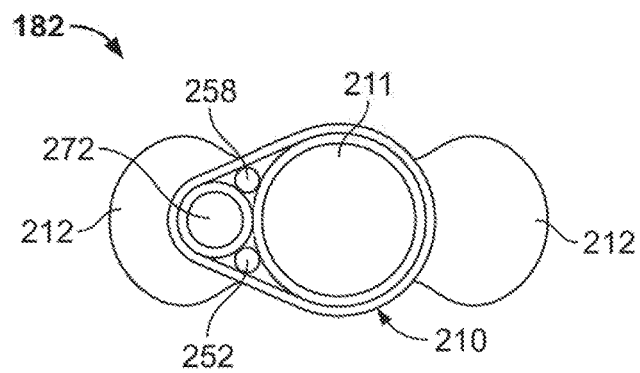

FIG. 9G illustrates a front view of the access device 182 of FIG. 9F. As shown, the access device 182 includes a working channel 211, an additional working lumen 272, an inflation lumen 258 coupled to the expandable members 212 and an aspiration lumen 252. In one variation, the multi-lumen access device 182 may be fabricated from a plurality of tubes having a covering or coating that defines the outer surface of the elongate member 210. As illustrated, the device 182 may include multiple expandable members 212 located at a distal end.

Figure 9H:
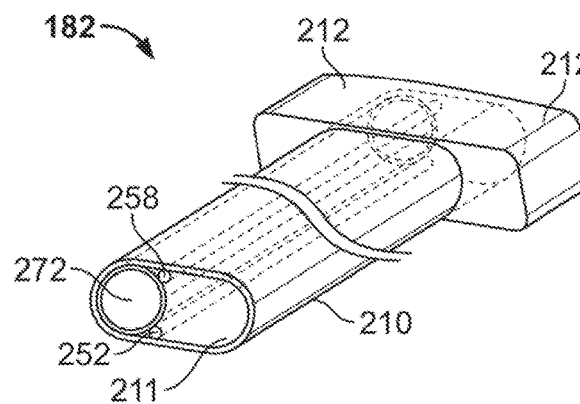
Figure 9I:
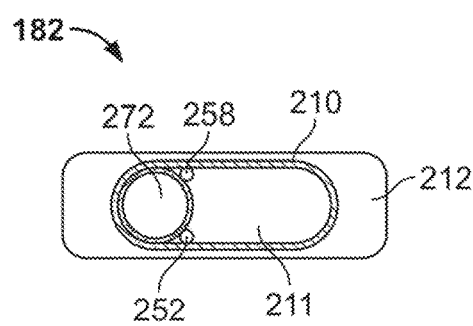

FIG. 9H illustrates another variation of an multi-lumen access device 182. As shown, the access device 182 may comprise an elongate member 210 having a passage to serve as the working channel 211. Separate tubes or similar structures may be placed within the working channel 211 to form a working lumen 272, aspiration 252, and inflation lumen 258. These lumens may also be formed using an extruded multi-lumen elongate member 210. FIG. 9I illustrates a rear view of the access device 182 of FIG. 9H. As shown, the expandable members 212 may be formed from a single balloon bladder located about the distal end of the device 182.

Figure 9J:
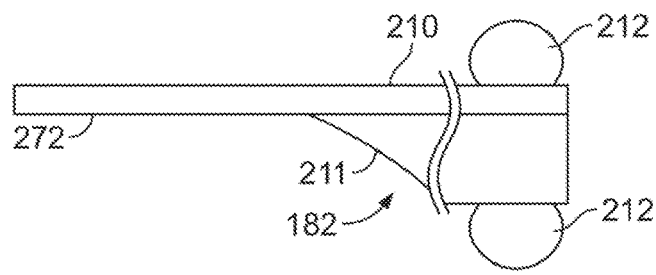
FIG. 9J show a variation of an access device where the working channel and second working lumen are offset at the proximal end of the device.

FIG. 9J show a variation of an access device 182 where the working channel 211 and second working lumen 272 are offset or staggered at the proximal end of the device 182. This configuration reduces interference between devices at the user end of the access device 182. Furthermore, the proximal end of the working channel 211 may be tapered along an end of the elongate member (as shown) to increase the area through which instrumentation enters the working channel 211.

FIGS. 10A to 10C show respective top, side, and bottom views of an access device 182 as described herein having both an expandable member 212 and separate stabilizers strands 216. As shown, the expandable member comprises a balloon 212 affixed to the elongate member 210 or guide tube. In this variation, the elongate member 210 has a non-circular cross-section defining a working channel 211 (e.g. elliptical, rectangular as shown, trapezoidal, or any other geometric shape). The working channel 211 allows for access to the temporary artificial cavity formed by the device. The elongate member 210 may be shapeable or have a particular curve as discussed herein. As noted above, in those variations where the guide tube maintains a curve, the curve will be selected depending on the desired surgical application. For example, to direct access from the skin incision/puncture on the abdominal side of the diaphragm, under the diaphragm and towards the posterior surface of the heart the access device 182 may have a distal portion that is curved or angled as shown in FIG. 10B.

In the variation shown in FIGS. 10A to 10C, the balloon is affixed along a planar side of the elongate member 210 such that the sides and bottom of the balloon are free and not attached. This configuration allows the balloon 212 to adjust to the spine, esophagus, and other structures while separating the heart with the stabilizer side of the elongate member 210. The stabilizer strands 216 may be fabricated to be malleable so that they fit around an organ and stabilize the organ during the procedure. For example, when used against the heart, the strands stabilize the heart as the balloon inflates to create the temporary cavity. The stabilizers 216 support the heart during manipulations of the instruments along the posterior surface of the heart or within the artificial cavity defined by the access device 182.

The stabilizer strands 216 are preferably fabricated from the elongate member 210 by cutting slots and preshaping the stabilizing features. However, the stabilizer may alternatively be fabricated from another component (e.g. spring metal such as spring steel or nitinol) covered with an atraumatic polymer and secured to the guide tube.

FIGS. 11A and 9B show an alternative access device 182 that incorporates expandable members comprising enlargeable strands 216 or stabilizers. The strands 216 may be preformed strands 216 or stabilizers fabricated from a spring material (e.g. a flexible polymer, spring stainless steel, nickel titanium, or other metal treated to meet the elastic requirements of the device). In some variations, the strands 216 assume a preshaped configuration upon deployment of the device. The strands 216 can be deformed during deployment to nest or separate the appropriate organ. The strands 216 may be malleable or resilient. For elastic or resilient strand configurations, the strands 216 have an expanded preshaped orientation. Wires may be used to retract the strands into a low profile. Once positioned, the wires may release the strands such that they expand radially outward into contact with the anatomy. In variations where the device is used to separate the heart from the esophagus, once both sets of strands are advanced, the strands separate the heart from the spine and esophagus, providing a temporary cavity in which instruments can be inserted and scopes can provide direct visualization, (e.g., as shown in FIGS. 8A to 8C).

In alternate variations, the strands 216 are actuated into an enlarged configuration upon positioning of the device. In the variation shown in FIG. 11B, the strands 216 can be actuated to cause advancement or retraction of the strands. As shown, one end of the strand may be affixed to the elongate member 210, while the other end may be advanceable within the elongate member. It should be noted that the strands may be individually enlarged to permit selective separation of the heart thereby lifting one side of the heart and rotating the heart to access the lateral surfaces and even the anterior surface of the heart. Furthermore, the strands 216 may be of different sizes as shown in FIG. 11A where the strands on the top of the device have a smaller expanded profile than the strands on the lower portion of the device.

In most variations, the stabilizing strands 216 designed to be atraumatic. For example, there may be a covering that prevents abrading or cutting of the anatomy that is separated by the strand 216. The space between the two sets of strands can be set based on the anatomic and/or procedure requirements.

FIGS. 11C and 11D show another variation of an access device 182 comprising a balloon 212 surrounding two expandable strands 216. It should be noted that any number of expandable strands can be used. The balloon 212, in this configuration, is attached to the strands and defines a free balloon along the side opposite to the strands. As such, when the strands 216 expand they enlarge the balloon and contact the spine region to provide a stabilizing point. As the balloon inflates using inflation media delivered through the inflation lumen 214, the balloon also surrounds the organ being separated. This function provides an atraumatic surface while separating and stabilizing the organs. For example, as the balloon inflates to separate the heart from adjacent organs, inflation of the balloon forms an atraumatic surface to support the heart. It should be noted that this variation of the device 182 may also be used when rotated 180 degrees so the expandable strands support the heart and the free side of the balloon contacts the spine and esophagus. The balloon is attached to the guide tube distal and proximal to the strands to define a fluid impervious bond. It should be noted that the two strands may be individually actuated to permit selective separation of the heart thereby lifting one side of the heart and rotating the heart to access the lateral surfaces and even the anterior surface of the heart.

Figure 12C:
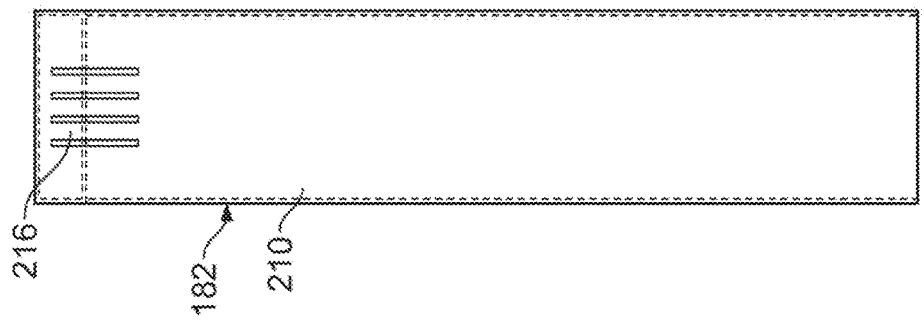
FIGS. 12A to 12C show a top view, a side view, and a bottom view of an access device having multiple stabilizer strands as expanding and stabilizing members.
Figure 12B:
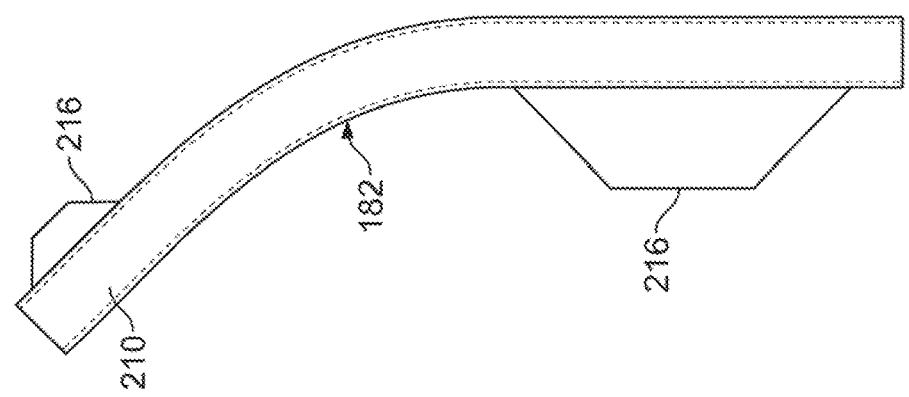
Figure 12A:
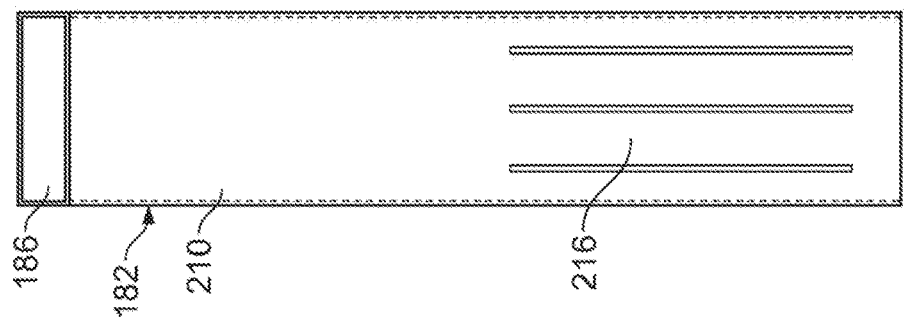

FIGS. 12A to 12C show an alternative variation of an access 182 where an expandable member comprises two sets of enlargeable strands 216, one set located towards a distal end of the device and a second set located proximally on the elongate member 210. The strands 216 may operate in any manner as described above. Variations of the device include sets of strands 216 that are offset either axially or radially from each other.

Figure 13B:
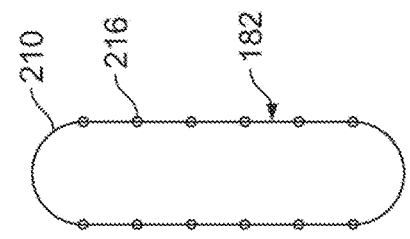
FIGS. 13A and 13B show a top view and a front view of an access device when the stabilizer members are in a compressed, low profile configuration.
Figure 13D:
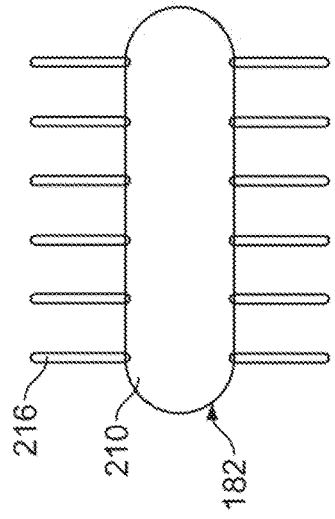
FIGS. 13C and 13D show a side view and a front view of the access device of FIGS. 13A and 13B in an expanded configuration.
Figure 13A:
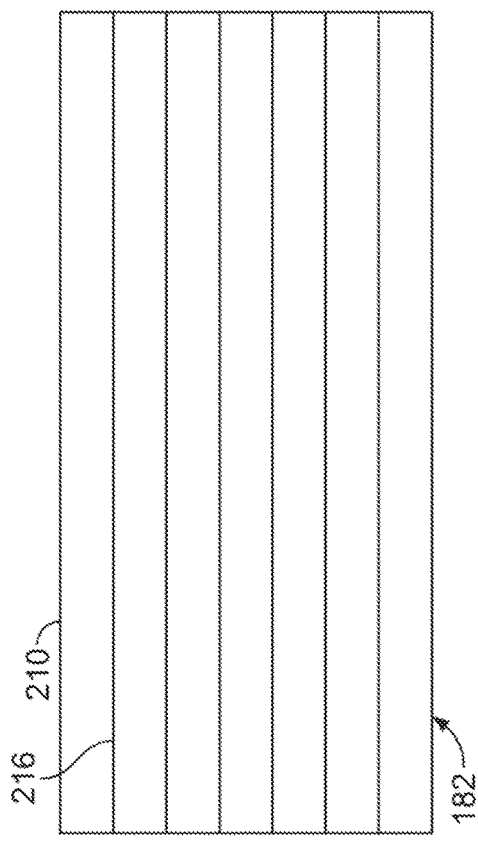
Figure 13C:
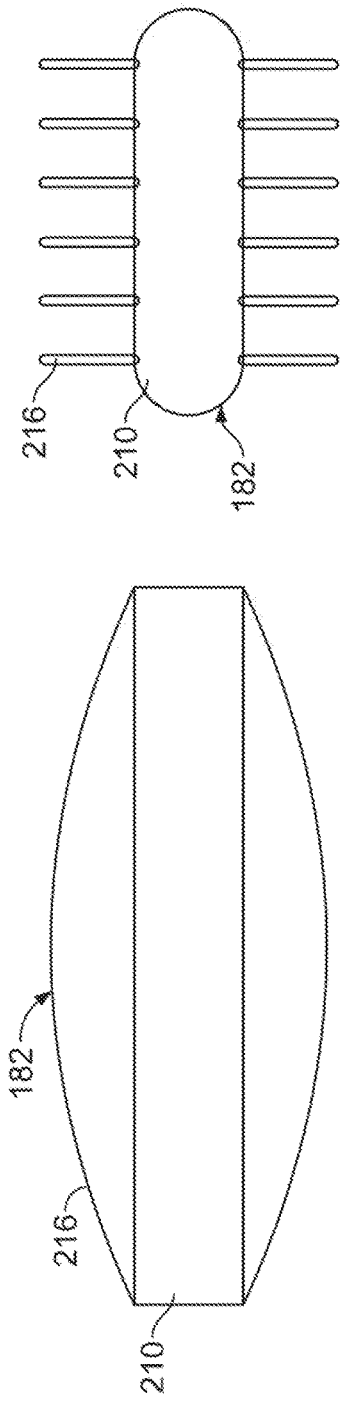

FIGS. 13A and 13B show an end portion of an access device 182 that comprises a series of enlargeable strands 216 along two sides of the elliptical elongate member 210. FIG. 13B shows the strands 216 in a compressed, low profile configuration. FIGS. 13C and 13D show a side and front view respectively of the access device 182 of FIGS. 13A and 13B. As shown, the strands are in an enlarged, expanded configuration. Again, the strands can be expanded as described above and define stabilizing surfaces to support the adjacent organs that are separated to produce the temporary cavity.

Figure 14A:
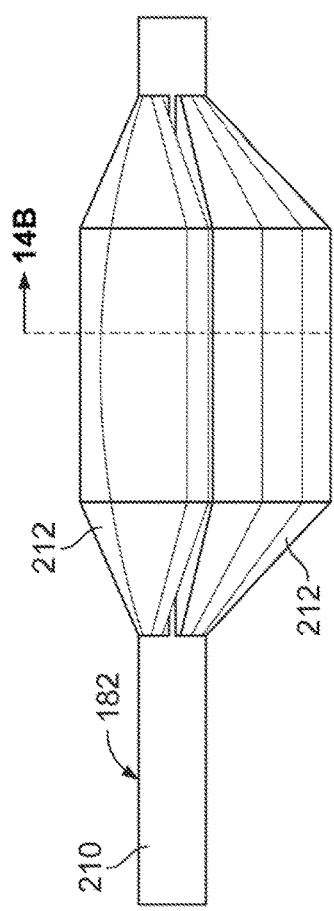
FIGS. 14A to 14C show a side view, an end view, and an isometric view of an access device having multiple balloons.
Figure 14C:
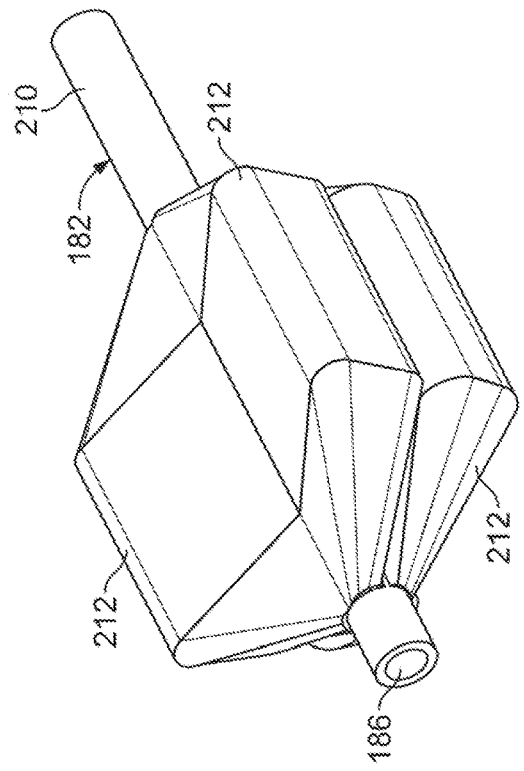
Figure 14B:
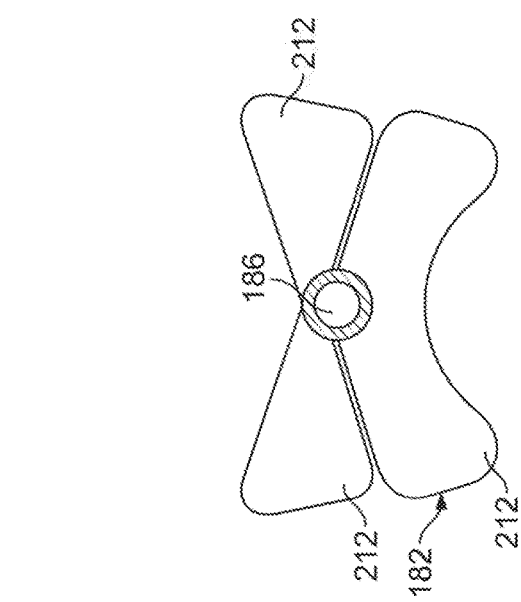

FIGS. 14A to 14C show another variation of an access device 182. In this variation, the device 182 incorporates three balloons 212 where two balloons 212 are oriented along the top of the elongate member 210 and a single balloon 212 is located at the bottom of the elongated 210. As shown, the balloons 212 may have pre-determined shapes that are useful when performing various procedures. For example, the bottom balloon 212 has a semi-circular groove on a surface that is opposite to the elongate member. This groove permits nesting of various organs (e.g., the spine or the esophagus) when creating the temporary cavity.

Figure 14D:
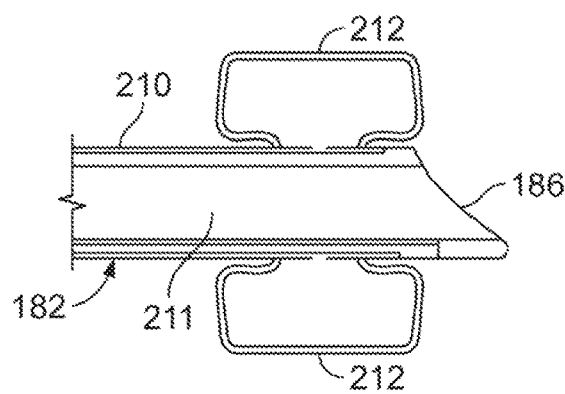
FIGS. 14D to 14J show additional variations of access devices.
Figure 14E:
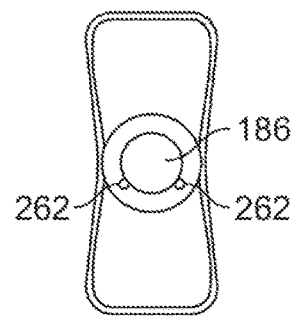
Figure 14F:
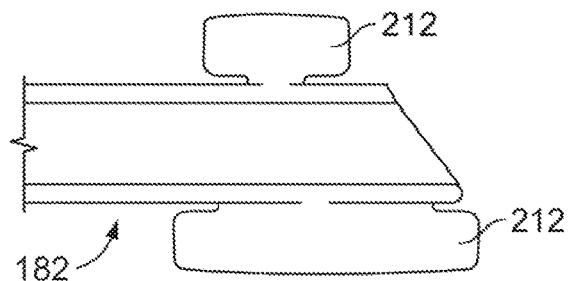
Figure 14G:
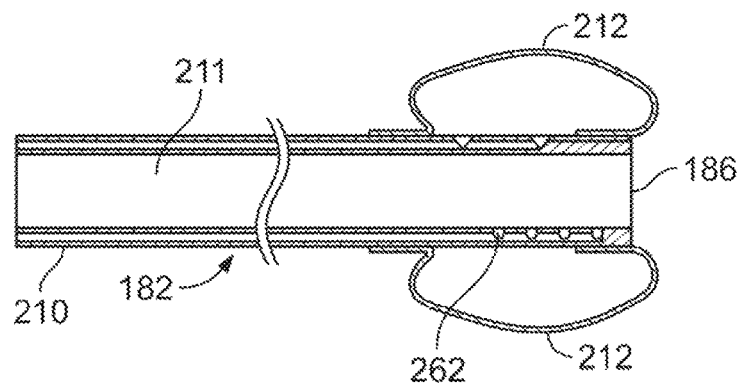

FIGS. 14D to 14F illustrate another variation of an access device 182. In this variation, the balloons 212 are selected to have a rectangular cross section when viewed co-axially along the elongate member 210 (as shown in FIG. 14D). Balloon 212 for use with the present device 182 may have any type of cross-section. As described below, the balloons may have varying shapes to accommodate certain organs or to create clearance at the opening 186 of the device 182. Such balloons may be pre-formed to a specific shape or cross-section. Furthermore, non-distensible balloons may also be employed with variations of the device.

FIG. 14D also shows the distal end of the elongate member 210 as being curved or angled to allow for a larger opening 186. Such a configuration permits greater access to the surface of the organ adjacent to the temporary cavity. As discussed above, the elongate member 210 may further include a plurality of aspiration/suction ports 262 located at an end of the device.

FIG. 14F illustrates yet another variation of an access device 182 where a length of one balloon member 212 is greater than the length of a second balloon member 212. Such a difference in length may be selected depending upon the desired procedure. In an alternate variation, a single balloon 212 may be employed where a portion of the balloon on one side of the elongate member 210 is shorter/longer than a portion of the same balloon on another side of the elongate member 210.

FIG. 114G shows a variation of an access device 182 where at least a portion of the balloon members 212 extend beyond the opening 186 of the elongate member 210. This configuration assists in spacing tissue from the opening 186 and reduces the probability that the tissue would otherwise obscure the visualization element (e.g., an endoscope) within the working channel 211 of the device 182. As shown, the device 182 may further include suction or aspiration ports 262 within the working channel 211 of the device and adjacent to the opening 186.

Figure 14H:
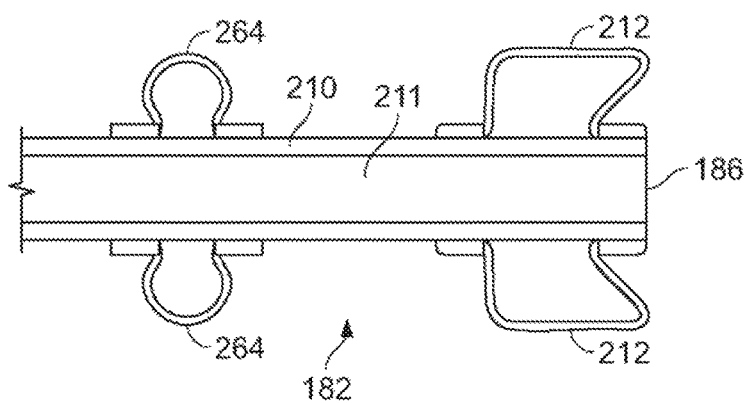
Figure 14I:
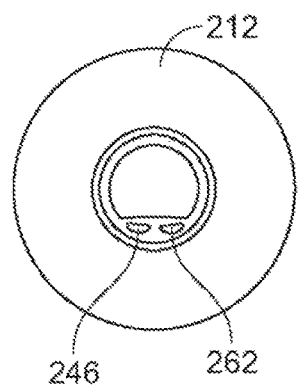
Figure 14J:
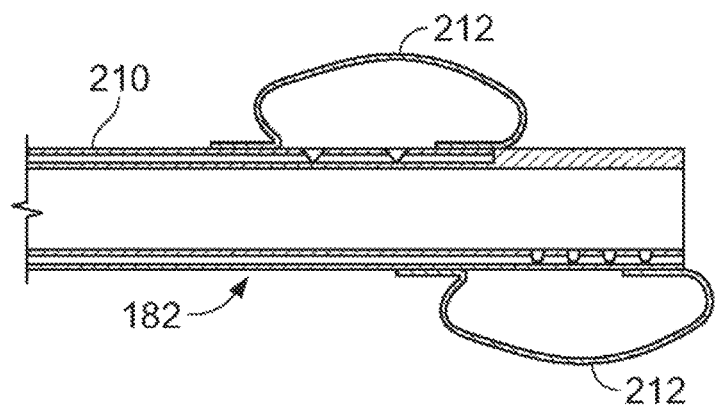

FIG. 14H illustrates a variation of an access device 182 in which the profile of the balloons 212 allows for clearance around the opening 186 of the working channel 211. Accordingly, a length of the balloon 212 adjacent to the elongate member 210 is less than a length of the balloon 212 at a surface away from the elongate member 212. FIG. 14H also shows a variation of the access device 182 as having locking members or balloons 264. The locking balloons 265 may be spaced from the distal end of the device 182 sufficiently so that upon inflation, they secure the device at the site by expanding within the body or outside of the body at the site of the incision. FIG. 14J shows a front view of the access device 182 of FIG. 14H. As shown, the end of the device 182 may include a suction/aspiration port 262 and a visualization/illumination element 246 that are spaced away from surrounding tissue due to the construction of the balloon 212.

FIG. 14J illustrates another variation of an access device 182 where the balloon members 212 are axially spaced along the elongate member 210.

Figure 15A:
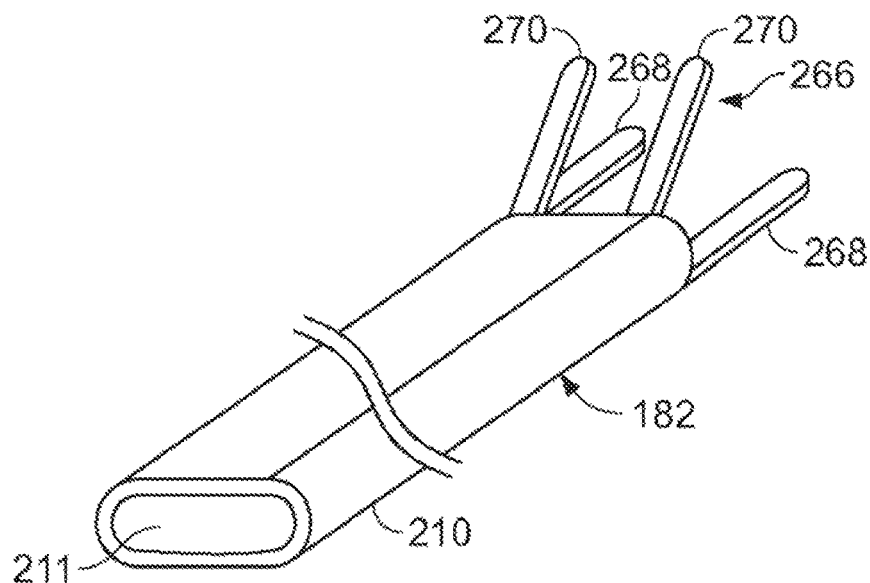
FIGS. 15A to 15C and 16A to 16B show additional variations of an access device where the expandable member is slidable out of the elongate member.
Figure 15B:
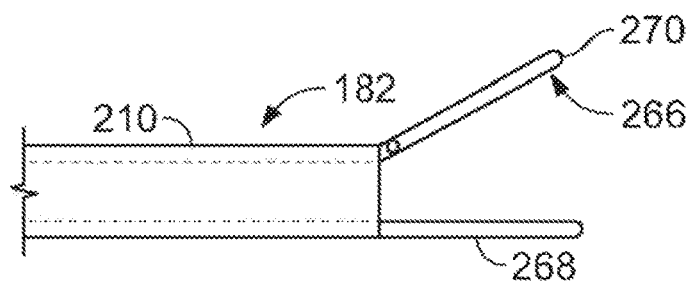
Figure 15C:

FIGS. 15A to 15C illustrates a variation of an access device 182 having an expandable member 266 that is slidable within the working channel 211 of the elongate member 210. As the expandable member 266 advances out of the elongate member 210, the expandable member expands in a manner that elevates and separates organs. As shown, the expandable member of FIG. 15A comprises a first and second set 268, 270 of arms. In this variation, the sets of arms 268, 270 expand in a non-uniform manner about the elongate 210 member. FIG. 15B shows a side view of the access device of FIG. 15A when the first and second set 268, 270 of the arms extends from the elongate member.

FIG. 15C shows the first and second set 268, 270 of arms retracted within the elongate member 210.

Figure 16A:
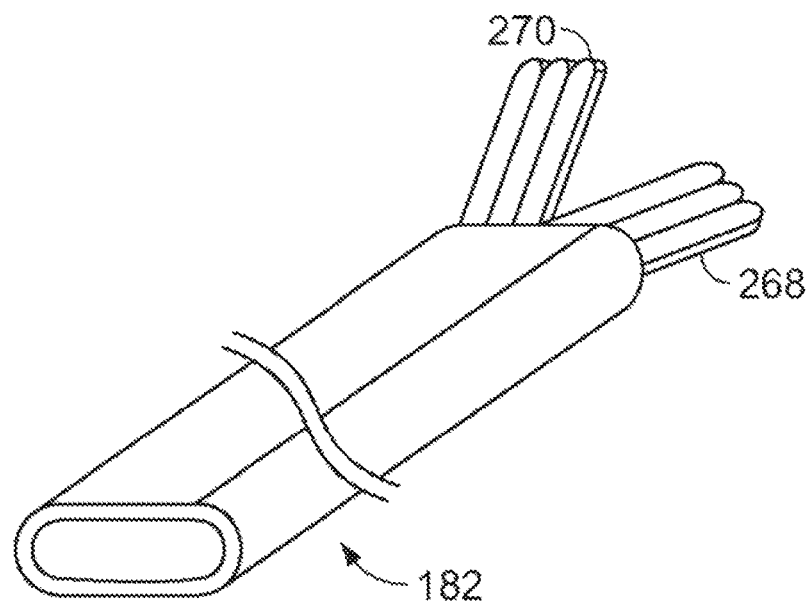
Figure 16B:
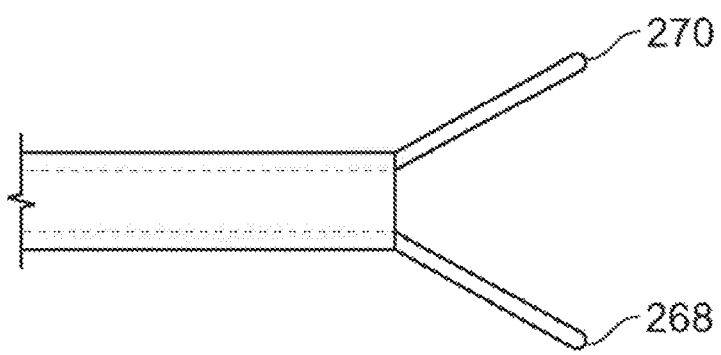

FIGS. 16A to 16B illustrate a variation of the access device 182 similar to the one shown in FIGS. 15A to 15C. However, in this variation, the access device 182 includes a first and second set 268, 270 of arms without spacing between the individual arms.

Figure 17B:
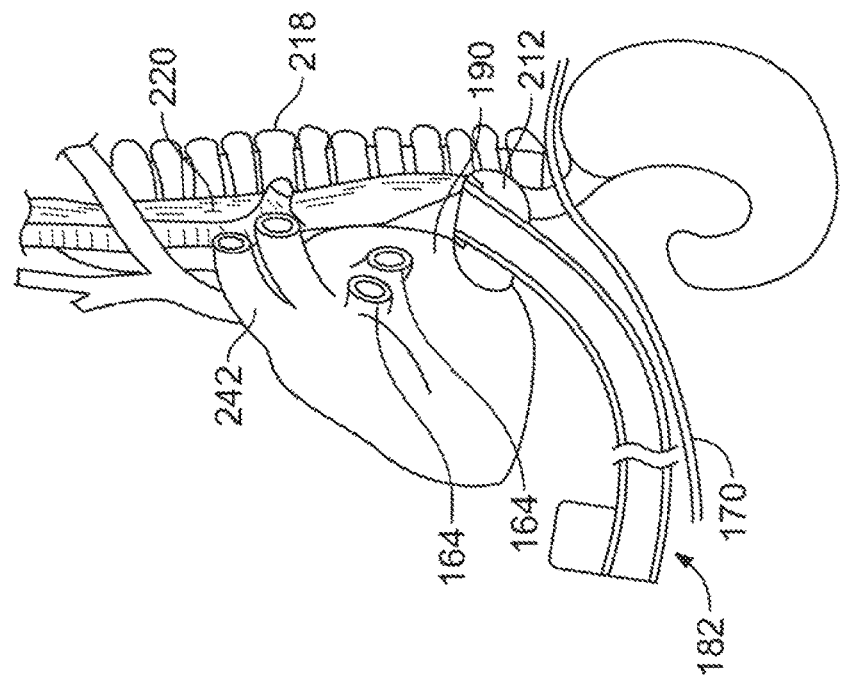
FIGS. 17A to 17B show an additional variation of an access device that is configured for use in a variety of traditional entry procedures.
Figure 17A:
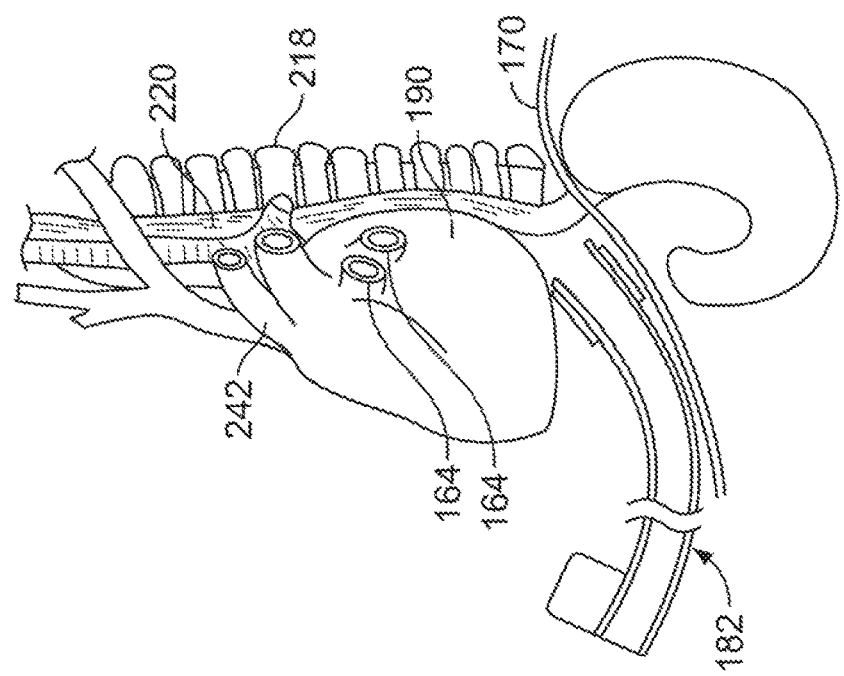

FIGS. 17A to 17B illustrate yet another variation of an access device 182. As shown in FIG. 17A, an access device 182 may also be used in parts of the body apart from the DEPA process. In this variation, the access device 182 has a curved shape to assist in positioning of the device 182 when advanced directly into the chest cavity during, for example, a sub-xyphoid approach as opposed to through the diaphragm 170. The shape of the access device 182 will vary depending on the procedure and intended entry procedure. As shown in FIG. 17B, once positioned, the expandable members 212 of the access device 182 may be inflated to elevate and separate organs to form a temporary cavity. Accordingly, variations of the present access devices 182 include elongate members that are curved, shapeable, or flexible to accommodate placement through the traditional entry techniques mentioned above.

Figure 18A:
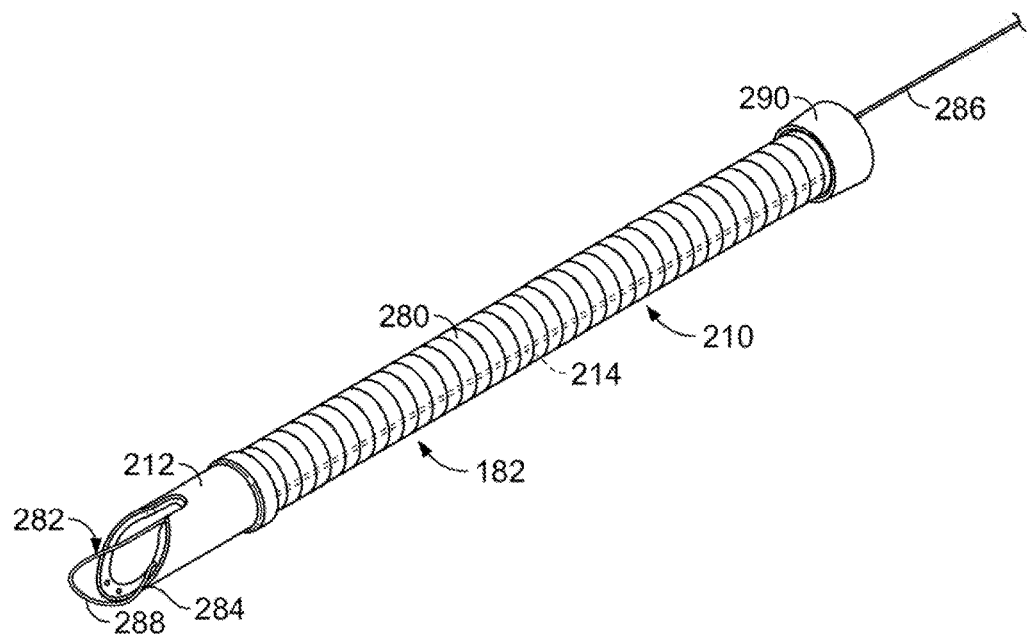
FIGS. 18A to 18C illustrate additional aspects of the access devices as described herein.

FIG. 18A shows additional features for use with access devices described herein. The illustration shows an access device 182 having an expandable member at a distal end of an elongate member 210. As shown, the elongate member may have a reinforcing member 282 extending over all or a portion of the elongate member 210. While the illustrated reinforcing member 282 is external to the elongate member 210, it may be located interior to, exterior to, or within the walls of the elongate member 210. The reinforcing member 282 may be a braided support, a coiled support, a mesh support or any such type of support that reinforces the elongate member 210. Although not illustrated, the access device 182 may optionally have any number of handles, or other features that allow manipulation of the device.

FIG. 18A also shows a rail-member 282 extending through the access member 182. The rail-member 282 can be a coiled guide-wire, an atraumatic guide-wire, polymeric strand or tube, or any similar structure. In use, the rail-member 282 has a portion that is affixed relative to the elongate member 282 and an axially moveable portion that extends within the elongate member 210. In most cases, the rail-member should not cause trauma to the intended region of tissue. For example, if use near cardiac tissue, the rail-member should be of a sufficient diameter so that it does not inadvertently cut or damage cardiac tissue.

Typically, the far portion 284 of the rail-member 282 is affixed to within the elongate member 210 so that distal movement of the remaining portion of the rail-member 282 causes an intermediary or mid-portion of the rail-member 282 to assume an arcuate profile, shape or perimeter (hereafter referred to as an arcuate profile) 288. In this variation, the shape formed is a semi-circular open-ended profile. However, the rail-member 282 can be fabricated to form any number of shapes. For example, the entire rail-member or a portion of the rail-member may have a pre-determined profile such that advancement of the rail-member out of the access device 182 causes the rail-member to assume the profile. In addition, the profile may be any geometric shape desired.

In the variation shown, the rail-member 282 is affixed to an inflation lumen 214 of the elongate member 210. However, the rail-member 282 may be affixed anywhere within or outside of the elongate member 210. Furthermore, while the rail-member 282 is shown as extending through the elongate member 210, additional variations include rail-members extending exterior to (or partially exterior to) the elongate member 210.

FIG. 18A also illustrates the access device 182 as having a valve 290. In one variation, the valve 290 may be a duck-bill valve that partially extends within the working lumen of the elongate member 210. Such a valve closes around the item being passed through the working channel. However, any type of valve can be used depending on the desired application.

Figure 18B:
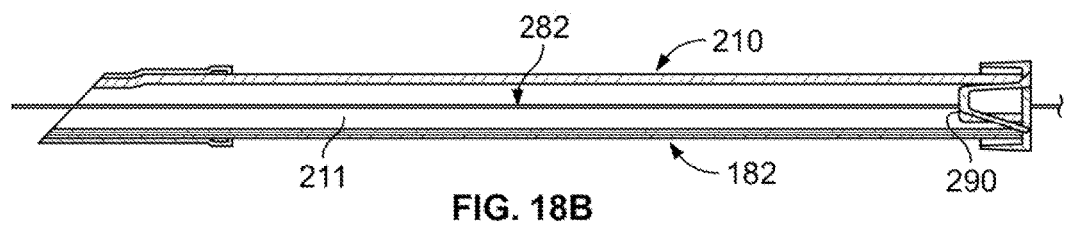

FIG. 18B illustrates a cross sectional view of the access device 182 of FIG. 8A. As shown, the rail-member 282 extends through the working channel 211 and through a valve 290 (in this case a duckbill valve) at the proximal end of the elongate member 210. Generally, the rail-member 282 is fabricated from a material such as a shape-memory alloy, a super-elastic alloy, metal alloy, polymer, or polymeric blend of materials. In most cases, the rail-member 282 is intended to function as a rail for the advancement of various medical implements. As such, variations of the rail-member 282 may be constructed to have sufficient stiffness so that the profile of the mid-section 288 stays substantially within a single plane. Naturally, the orientation of the mid-section 288 can be manipulated by movement of the proximal or near end of the rail-member.

Figure 18C:
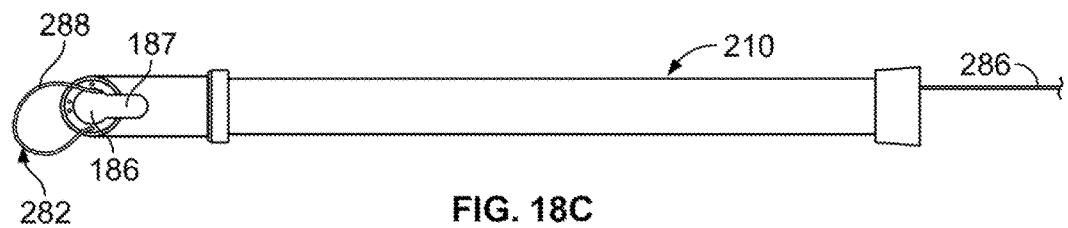

FIG. 18C shows a top view of the access device 182 of FIG. 18A. As discussed above, access devices 182 according to the present invention may include one or more slots 187 adjacent to the opening 186 at the distal end of the elongate member 210. This slot 187 has been particularly useful to manipulate/rotate instruments within the working channel 211. In the variation shown, the expandable member 212 is formed round the slot 187 so that upon expansion, the expandable member 212 does not occlude the temporary cavity space that is adjacent to the slot 187.

Figure 19A:
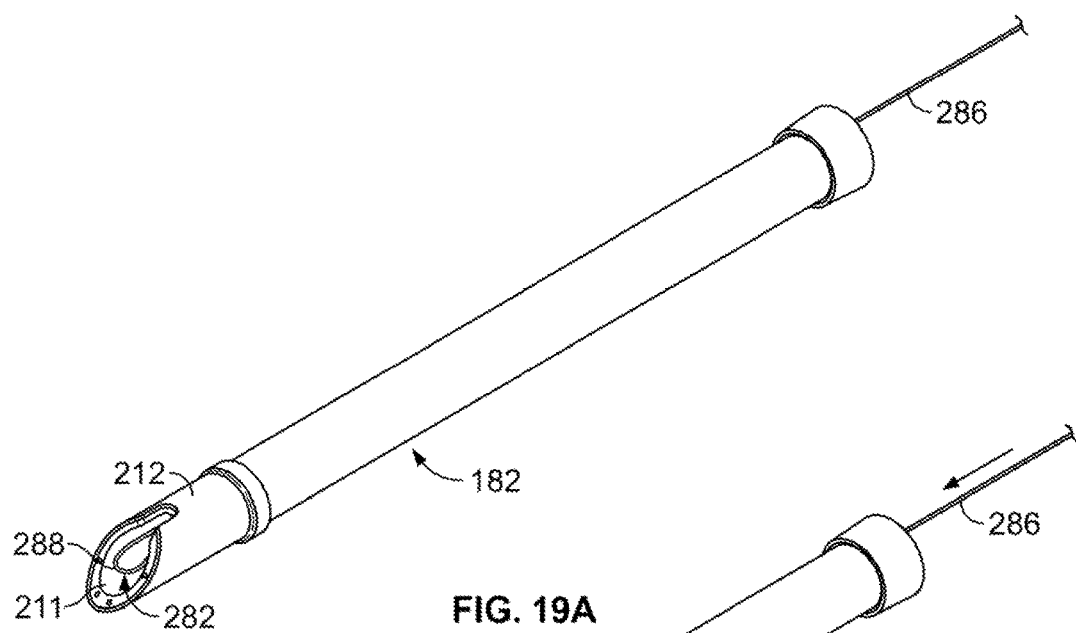
FIGS. 19A to 19C show a rail-member of the access device advancing out of the access device and a treatment device being advanced over the rail-member.

FIG. 19A shows an example of the rail-member 282 in use. For purposes of illustration, the expandable member 212 is not shown in an inflated position. During use of the device, the expandable 212 member may be fully or partially expanded. Alternatively, the expandable member 212 need not be expanded during use. As shown, the mid-section 288 of the rail-member 282 remains within the device 182. Also, in this illustration, the far end of the rail-member 282 is affixed within the working channel 211 of the access device 182.

Figure 19B:
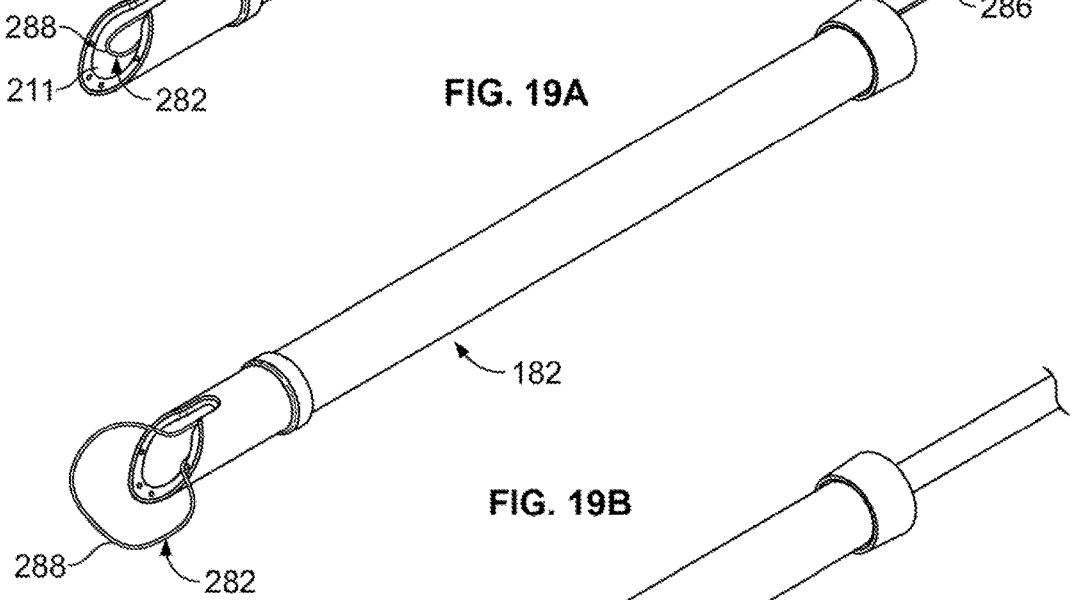

FIG. 19B illustrates axial movement of the rail-member 282, particularly distal movement of the near end 286 of the rail member 282. As the rail-member 282 advances, the mid-section 288 assumes an arcuate profile. As illustrated, the profile of the mid section 288 is shown to be an open-ended loop. However, any number of shapes is contemplated to be within the scope of this invention.

Figure 19C:
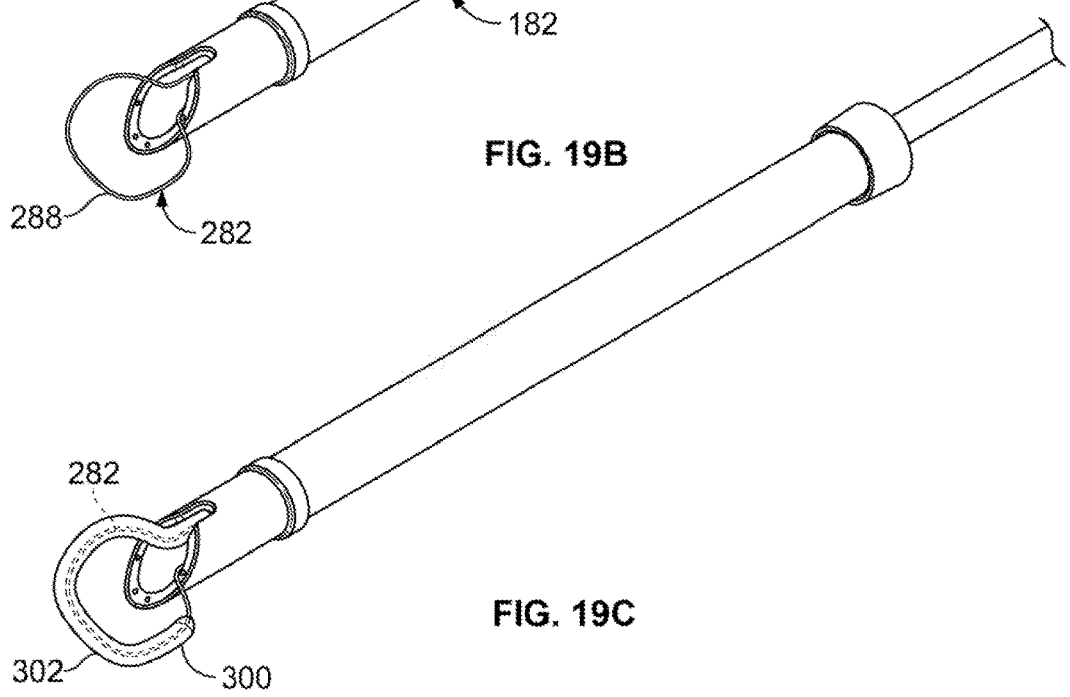

FIG. 19C shows the advancement of a treatment device 300 over the rail member 282. The treatment device 300 will include a rail-lumen or track allowing for the device 300 to advance along the rail-member 282 and ultimately take the shape of the profile of the mid-section 288. Although not limited to the pictured illustration, the treatment device 300 can include an electrode 302 for treatment of tissue. As shown, the electrode 302 may optionally also take the shape of the mid section 288. In use, the rail-member 282 is advanced out of the access device 182 while over the tissue to be treated. The rail-member 282 provides the ability of the medical practitioner to position treatment devices 300 with greater precision. The access device 182 with rail-member has also shown considerable promise in positioning treatment devices 182 over posterior regions of organs in the thoracic cavity as described herein.

Figure 20A:
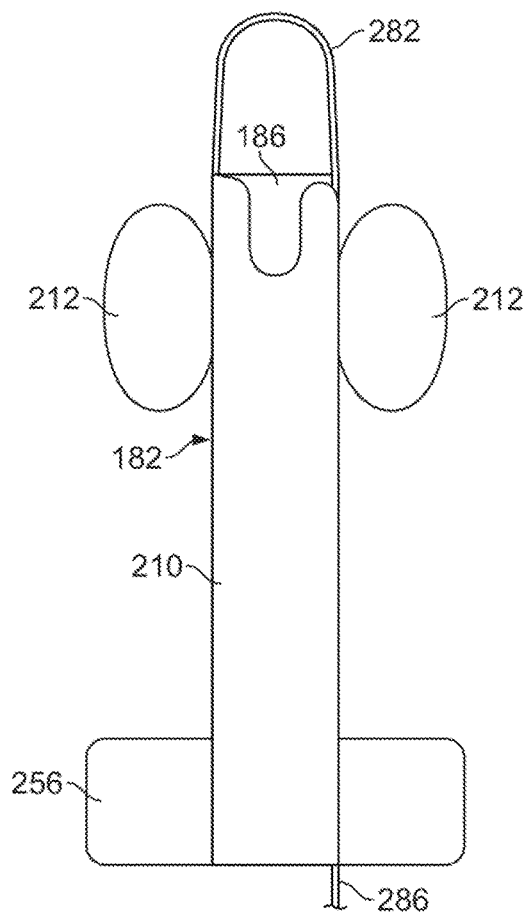
FIGS. 20A to 20B show additional variations of access devices having rail-members.
Figure 20B:
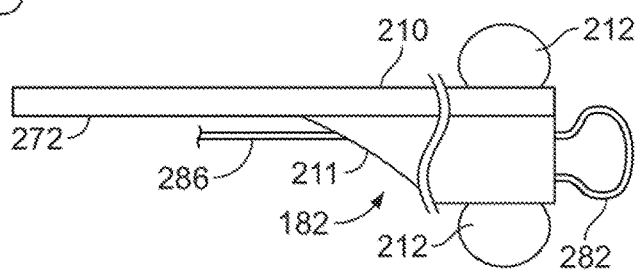

FIG. 20A illustrates another variation of an access device 182 as discussed above having handles 256 with the addition of a rail-member. In this variation, the rail-member 282 expands substantially distally to the opening 186 of the access device 182. FIG. 20B illustrates another variation of an access device 182 according to the present invention. In this variation, the access device 182 may include an additional working lumen 272 within the elongate member 210. The additional working lumen 272 in this variation is separate from the working channel 211 and provides an access channel having the ability to leave a device at the temporary cavity while advancing and/or removing other devices without causing undue interference between devices. In this variation, the rail member 282 is affixed within the working channel 211 of the device. However, the rail-member 282 may also be affixed to the additional working lumen 272.

The rail-member 282 may be a separate or separable from the body of the access device 182 and temporarily affixed into a lumen or receptacle in the access device 182 to provide a rail-type function over which treatment device can be advanced. This separate/separable feature permits use of a single rail-member that can be inserted into the working channel 211 of the access device 182 and can be used to guide the treatment devices to their intended location. In addition, the elongate member 210 of the access device 182 can incorporate one or more multiple lumens through which the rail member 282 can be advanced.

Figure 20C:
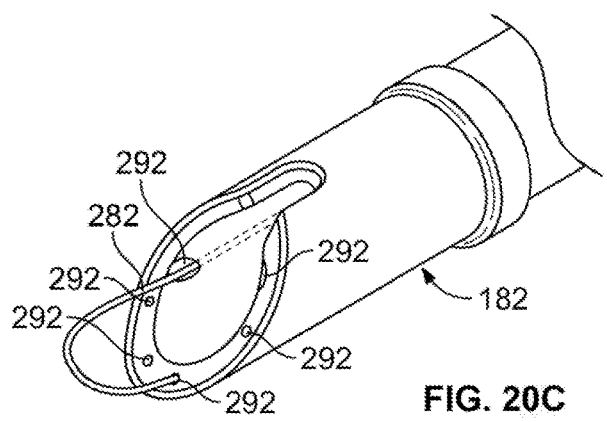
FIG. 20C shows features that allow a user to selectively locate a rail-member relative to an access device.

As shown in FIG. 20C, variations of the access device 182 may have one or more opening 292 to temporarily or permanently attach or advance a rail-member 282 The device 182 may have openings, apertures, notches or other such features in place of openings 292. Regardless, such openings 292 or other features that allows the user to change the location of the rail-member on or within the elongate member 211. In one example, such features allow for the user to change the shape of the loops created by the rail-member or to otherwise manipulate the rail-member relative to the access device 182. For example, in the example shown in FIG. 20C, the rail-member 282 expands in profile on the right side of the access device 282. However, by extending the rail-member 282 from or through another opening 282, the user can select how the rail-member 282 expands in profile.

Figure 21A:
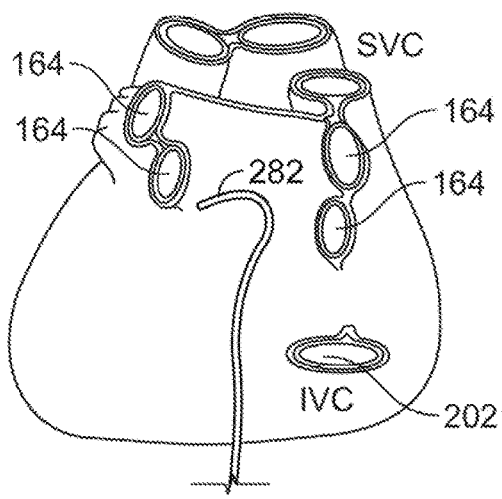
FIGS. 21A to 21C illustrates a rail-member advanced to a target site and an arcuate profile or path so that a treatment device can be advanced over the rail member for treatment of the tissue.
Figure 21B:
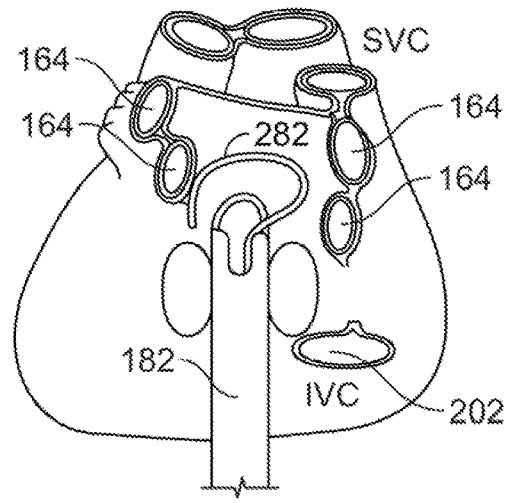
Figure 21C:
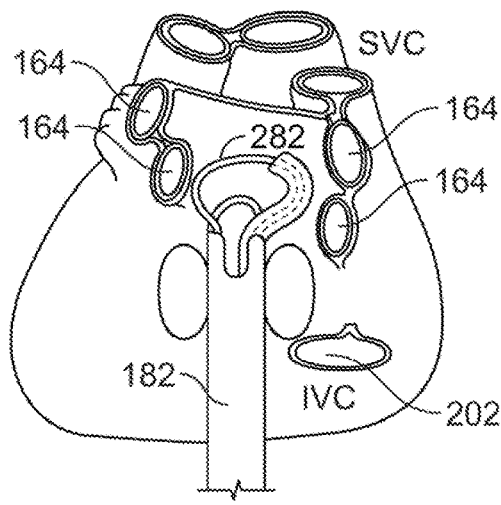

FIGS. 21A-21C illustrate the access devices 182, as described herein, when used in video assisted procedures such as pericardiac surgery or trans-abdominal pericardiac surgery. As noted previously, the access devices described herein allow for direct visualization and exposure to the posterior surface of organs within the thoracic cavity. The illustrated examples demonstrate how the access devices enable access to posterior regions of the heart for the creation of exterior Maze lesions. The use of the access device 182 also optionally allows a surgeon to create such lesions without dissection of the pericardial reflections (a line of folding along which the visceral pericardium becomes the parietal pericardium). This ability to create lesions without dissection of this tissue enables a faster procedure as well as improved recovery time. However, these devices may also have wider applications and, unless otherwise indicated, their uses are not limited to any particular type of surgery.

As shown, in FIG. 21A, a surgeon advances a guidewire or rail-member 282 to (or near) the intended treatment site. As shown, the rail-member 282 may be advanced by itself and subsequently joined with the access device 182. The placement of the rail-member 282 may rely on one or more additional guide-wires. Furthermore, the rail-member may have a floppy distal end (or both ends may be floppy.) As the distal end is placed along or near the target tissue, it may be fed into the access device 182. A treatment device, such as a coagulation device, can then be fed over the rail-member to apply the desired treatment.

In one example, when treating the heart, a surgeon may placing a guidewire that functions as the rail-member through an access location (port, incision, etc.), along the roof of the left atrium (after dissecting the superior vena cava, the aorta, and the pulmonary artery). Next, the surgeon advances the guide-wire along the anterior surface of the left pulmonary vein and into the access device. A coagulation device can then be fed over the guidewire to create the roof lesion and an anterior pulmonary vein lesion. The same or similar techniques may be used when placing the guidewire along the anterior right pulmonary vein to create right atrial or other lesions.

FIG. 21B illustrates advancement of an access device 182. Variations of the procedure include first advancing the access device 182 and positioning the access device (the expandable members may or may not be expanded) then advancing the rail-member through the access device. Once the rail-member is in a desired location, it may then be affixed or joined to the access device. Alternatively, the rail-member 282 may be positioned and then the access device can be positioned over the rail-member 282 at or near the target site. Ultimately, the rail-member 282 is affixed or joined to the access device 182. It will be apparent to those skilled in the art, that a medical practitioner may use surgical manipulation instruments to affix or join the rail-member 282 to the access device 182 when both are within the body.

FIG. 21C illustrates the rail-member 282 after affixing or joining with the access device 182. As noted above, once coupled to the access device 182, an end of the rail-member 282 can be manipulated by the medical practitioner to assume a profile or shape suited for guiding a treatment device. In some cases, the rail-member 282 itself may actually be used to grasp or cut tissue. However, in most variations, the edges of the rail-member are selected so as to be atraumatic to tissue as the medical practitioner positions the rail-member 282 within the body.

FIG. 21C also shows a treatment device 300 advanced over the rail-member 282. The rail-member 282 and/or treatment device 300 may then be manipulated to positioning the treatment device 300 over or on the tissue to create the desired lesion or treatment pattern.

Although the access devices described above are not limited in the devices that are advanced over the rail-member, it was found that ablation catheters having suction capabilities allowed for improved contact between the electrode and tissue being coagulated. In addition, it was found useful to include a lubricious material (such as a polyimide tube) when advancing the coagulation devices over the rail-member. In addition, such devices were constructed to have significant stiffness and torque characteristics to aid in manipulation of the devices at the target region.

Figure 22:
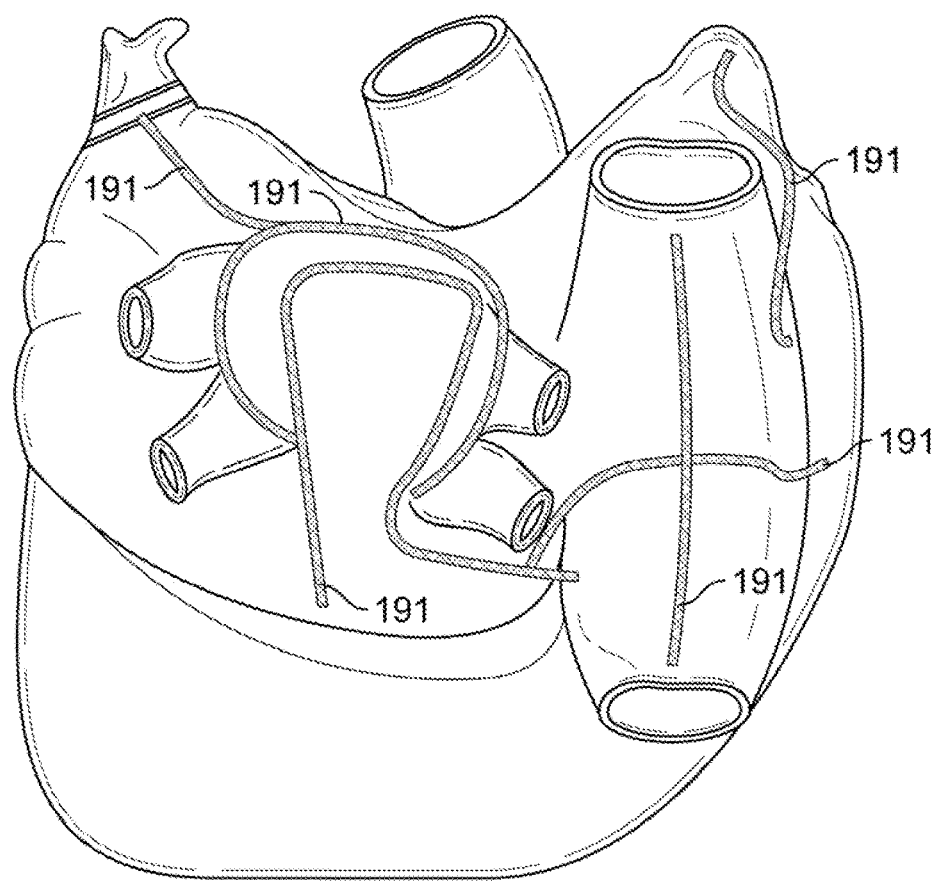
FIG. 22 illustrates an example of a lesion pattern created without dissection of pericardial reflections.

FIG. 22 illustrates one example of lesion patterns 191 created on a posterior surface of the heart using the access device and probes referenced herein. These lesion patterns 191 avoid the need to dissect pericardial reflections from the pulmonary veins because the devices allow for creating lesions along the pericardial reflections rather than through them.

FIGS. 23A to 23D show an additional variation of an access device 210 advanced through a diaphragm 170 to access a posterior region of the thoracic cavity. In this variation, the procedure also relies on one or more ports (as shown in FIG. 1C above) placed in a right chest area of a patient. The presence of the additional right port(s) allows for manipulation of devices from two points, the access device 210 and the right port. Accordingly, a variety of coagulation patterns can be formed.

Figure 23A:
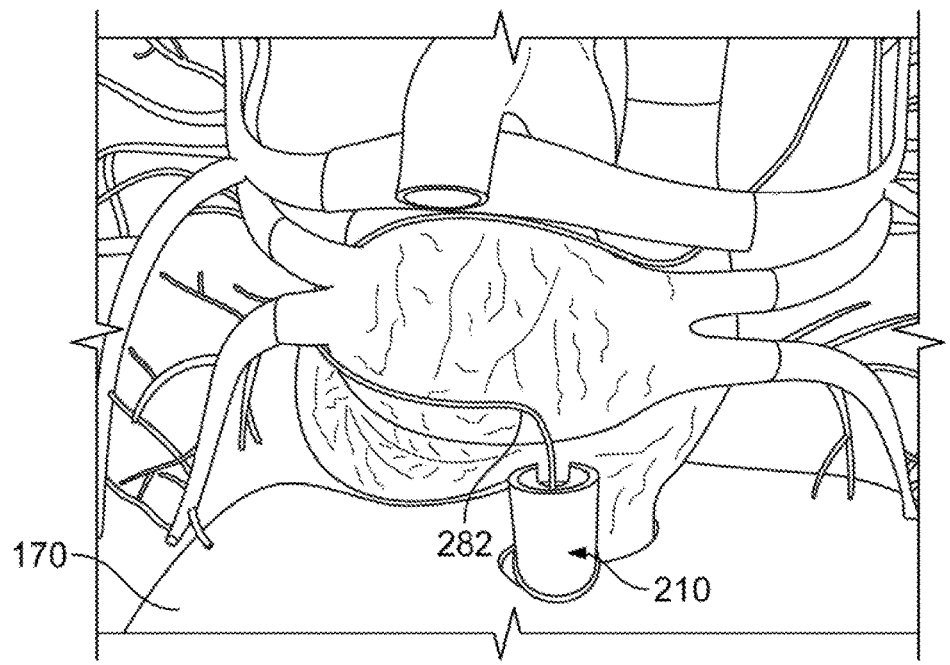
FIGS. 23A to 23D show additional variations of an access device advanced through a diaphragm to access a posterior region of the thoracic cavity.

If the variation shown in FIG. 23A, a surgeon can advance a guide wire 282 to the posterior surface of the heart, around the left pulmonary veins, back over the posterior atrial surface and then towards an anterior surface of the heart. Subsequently, though not shown, the surgeon can then advance a coagulation device over the guide wire 282 to form any number of coagulation patterns. The presence of the right ports (not shown) gives the surgeon the second access point (in addition to the access device 210 through which the guide wire 282 (or coagulation device) can be manipulated.

Figure 23B:
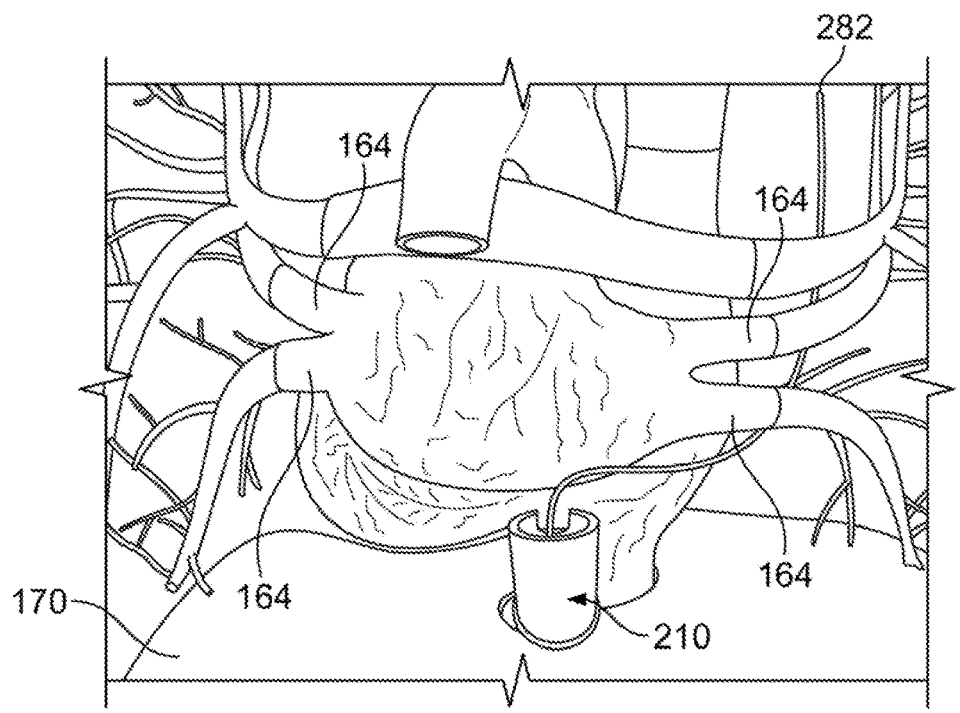

FIG. 23B illustrates another example where the guide wire 282 exits the access device 210 at the posterior region of the heart and then is manipulated behind the right pulmonary veins. Again, a surgeon can use the guide wire 282 to assist in placing a coagulation device to create one or more coagulation lesions on the epicardial surface. The guide wire 282 can be positioned back to the posterior surface or remain in the anterior region to create additional lesions.

Figure 23C:
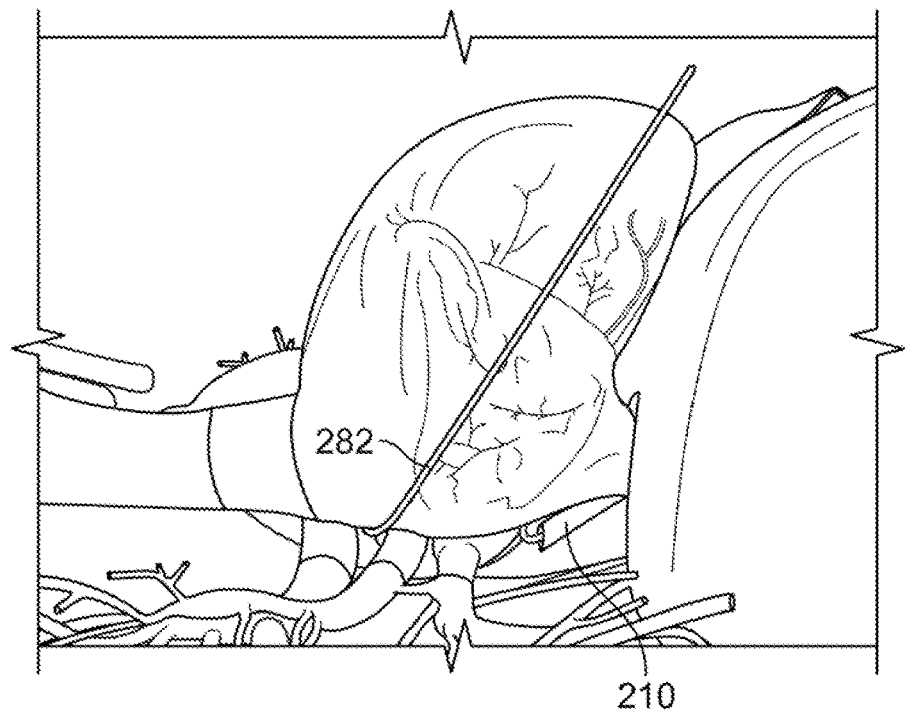
Figure 23D:
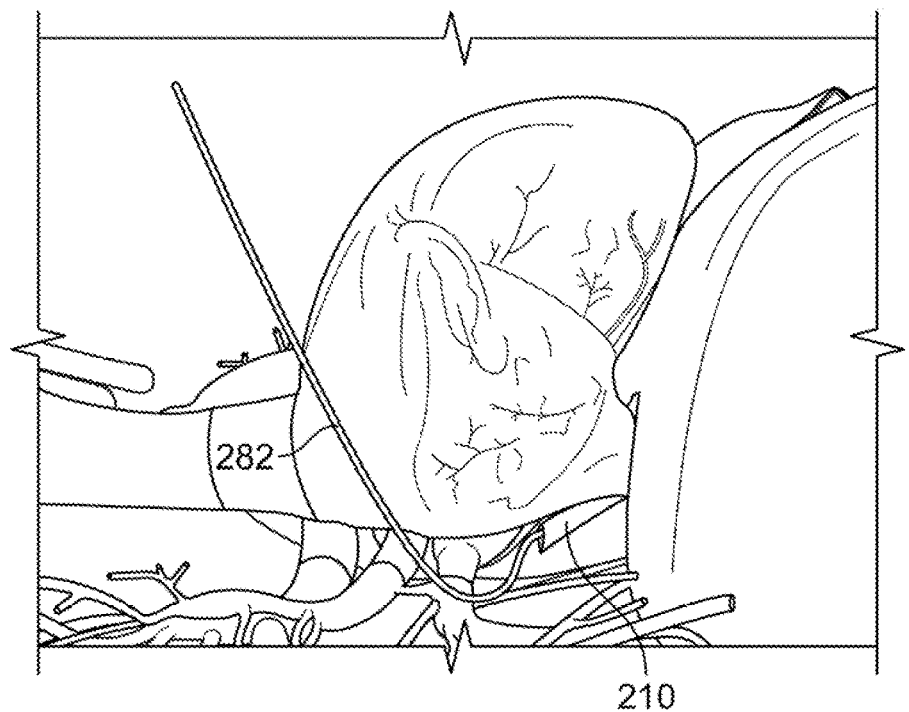

FIGS. 23C and 23D show a right view of the guide wire 282 when advanced as shown in FIGS. 23A and 23B respectively. As shown, the surgeon is able to manipulate the guidewire over the right atrial surface given the presence of right ports.

It is noted, that any number of lesion and patterns may be created depending upon the surgeon's preference and the type of procedure being performed. The combination of the access device 210 and the right access ports permits creation of exterior coagulation patterns/lesions on the epicardial surface without the need to dissect pericardial reflections. Furthermore, the lesions can be created on the reflections themselves. This dual access also allows for direct visualization and control when creating the lesions.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

Various kits can be sold that provide the practitioner with a complete system with which to perform a DEPA procedure. A separator/elevator, a coagulation device, an endoscope, a dissecting/tunneling instrument, trocars, a diaphragm patch, and staples to close the diaphragm opening may be incorporated into a kit used for atrial fibrillation or ventricular tachycardia treatment using a DEPA procedure.

What is claimed is:

1. A method of creating a treatment pattern in a target tissue, where the target tissue comprises a first tissue surface and a second tissue surface, where the second tissue surface is on an opposite side of the first tissue surface, the method comprising:
    positioning a first medical treatment device adjacent to the first tissue surface;
    forming a first portion of the treatment pattern along the first tissue surface using the first medical treatment device such that the first portion of the treatment pattern is incomplete;
    positioning a second medical device having at least one energy source adjacent to the second tissue surface;
    applying energy adjacent to the second tissue surface using the energy source;
    identifying a location of the energy source through the target tissue from the first tissue surface to locate the second medical device; and
    repositioning the second medical device on the second tissue surface in response to the location of the first portion of the treatment pattern and using the second medical device to form a second portion of the treatment pattern on the second tissue surface to complete the treatment pattern.

2. The method of claim 1, where the first medical treatment device comprises a first coagulation device.

3. The method of claim 2, where the second medical treatment device further includes at least one coagulation source.

4. The method of claim 2, further comprising advancing a second coagulation device to the target location to create the second coagulation lesion.

5. The method of claim 2, where the first coagulation device and the second medical device comprise opposite poles of an RF energy supply, and where energy flows between the first coagulation device and second medical device during application of the RF energy supply.

6. The method of claim 1, where the first medical treatment device comprises a device selected from the group consisting of an RF energy device, a laser device, an infrared heating device, a chemical ablation device, a cryogenic device, a microwave energy device, and a resistive heating device.

7. The method of claim 1, where the energy source comprises an energy selected from the group consisting of visible light, coherent light, ultraviolet light, magnetic energy, and electrical energy.

8. The method of claim 1, where identifying the energy source through the target tissue from the first tissue surface comprises placing a sensor device adjacent to the first tissue surface where the sensor device measures the energy to determine a proximity between the second device and the sensor device.

9. The method of claim 1, where the first tissue surface comprises an epicardial surface and the second tissue surface comprises an endocardial surface.

10. The method of claim 1, where the first tissue surface comprises an endocardial surface and the second tissue surface comprises an epicardial surface.

11. The method of claim 2, where the first, coagulation device is advanced through a port or trocar positioned in a body and where the second device is advanced through a vascular path in the body.

12. The method of claim 11, where the port or trocar is located in an abdominal wall of the body and the first coagulation device is advanced through the diaphragm.

13. The method of claim 12, where no ports or trocars are positioned in a chest wall of the body.

14. The method of claim 12, where the first coagulation device is positioned adjacent to the first cardiac surface without requiring deflation of a lung.

15. The method of claim 11, where the port or trocar is located in a chest wall of the body and the first coagulation device is advanced through the diaphragm.

16. The method of claim 1, further comprising advancing a scope into a body where the scope comprises at least one visualization element and where identifying the location of the energy source through the target tissue from the first tissue surface to locate the second device comprises using the visualization element to identify the location of the electromagnetic energy.

* * * * *